United States Patent [19]

Topfer et al.

[11] Patent Number: 5,910,631
[45] Date of Patent: Jun. 8, 1999

[54] **MIDDLE CHAIN-SPECIFIC THIOESTERASE GENES FROM *CUPHEA LANCEOLATA***

[75] Inventors: Reinhard Topfer, Bergheim; Norbert Martini; Jozef Schell, both of Cologne, all of Germany

[73] Assignee: Max-Planck-Gesellschaft zur Forderung der Wissenschaften E.V., Munich, Germany

[21] Appl. No.: 08/605,106

[22] PCT Filed: Sep. 2, 1994

[86] PCT No.: PCT/EP94/02935

§ 371 Date: Sep. 23, 1996

§ 102(e) Date: Sep. 23, 1996

[87] PCT Pub. No.: WO95/06740

PCT Pub. Date: Mar. 9, 1995

[30] Foreign Application Priority Data

Sep. 3, 1993 [DE] Germany .............................. 43 29 828

[51] Int. Cl.⁶ ................. A01H 5/00; C12N 5/14; C12N 15/29; C12N 15/52; C12N 15/82
[52] U.S. Cl. ...................... 800/298; 435/320.1; 435/419; 435/468; 435/469; 435/470; 536/23.2; 536/23.6; 800/281
[58] Field of Search .................................. 536/23.2, 23.6; 435/172.3, 320.1, 419; 800/205, DIG. 9

[56] References Cited

U.S. PATENT DOCUMENTS 5,455,167 10/1995 Voelker et al. ....................... 435/172.3

FOREIGN PATENT DOCUMENTS

| | | | |
|---|---|---|---|
| 91/16421 | 10/1991 | WIPO | .............................. C12N 9/14 |
| 92/11373 | 7/1992 | WIPO | ............................. C12N 15/55 |
| 92/20236 | 11/1992 | WIPO | ............................... A23D 7/00 |
| WO 92/20236 | 11/1992 | WIPO | . |
| 94/10288 | 5/1994 | WIPO | . |
| WO 94/10288 | 5/1994 | WIPO | . |
| 95/07357 | 3/1995 | WIPO | ............................ C12N 15/82 |

OTHER PUBLICATIONS

Dehesh, K., et al., "Two Novel Thioesterases are Key Determinants of the Bimodal Distribution of Acyl Chain of length Cuphea palustries Seed Oil", *Plant Physiology*, 110, 203–210, (1996).
S A Bayley, et al., "Metabolic Consequences of Expression of the Medium Chain Hydrolase Gene of the Rat in Mouse NIH 3T3 Cells", *Biotechnology*, 6, 1219–1221, (Oct., 1988).
P Dormann, et al., "Characterization of Two Acyl–Acyl Carrier Protein Thioesterases from Developing Cuphea Seeds Specific for Medium–Chain–and Oleoyl–Acyl Carrier Protein", *Planta, 189*, 425–432, (1993).
P Dormann, et al., "Characterization of Two Acyl–Acyl Carrier Protein Thioesterases from Developing Cuphea Seeds Specific for Medium–Chain–and Oleoyl–Acyl Carrier Protein", *Biological Abstracts 96*, Abstract No. 9558, (1993).

A Hellyer, et al., "Induction, Purification and Characterization of Acyl–ACP Thioesterase from Developing Seeds of Oil Seeds of Oil Seed Rape (*Brassica napus*)", *Plant Molecular Biology, 20*, 763–780, (1992).
H Imai, et al., "Acyl–(Acyl–Carrier Protein) Hydrolase from Squash Cotyledons Specific to Long–Chain Fatty Acids: Purification and Characterization", *Plant Molecular Biology, 20*, 199–206, (1992).
D S Knutzon, et al., "Isolation and Characterization of Two Safflower Oleoyl–Acyl Carrier Protein Thioesterase cDNA Clones", *Plant Physiology, 100*, 1751–1758, (1992).
N M Loader, et al., "Isolation and Characterization of Two *Brassica napus* Embryo Acyl–ACP Thioesterase cDNA Clones", *Plant Molecular Biology, 23*, 769–778, (1993).
N Martini, et al., "Thioesterase Genes for the Biosynthesis of Medium Chain Fatty Acids in Seeds of *Cuphea lanceolata*", *Biol. Chem. Hoppe–Seyler, 374*, Abstract No. PL35, p. 531, (1993).
T A McKeon, et al., "Purification and Characterization of the Stearoyl–Acyl Carrier Protein Desaturase and the Acyl–Acyl Carrier Protein Thioesterase from Maturing Seeds of Safflower", *J. Biol. Chem., 257*, 12141–12147, (1982).
C M Miyamoto, et al., "Organization of the lux Structural Genes of *Vibrio harveyi*", *J. Biol. Chem., 263*, 13393–13399, (1988).
A Muller, et al., "Isogenes of the Thioesterase from *Cuphea lanceolata*", *Biol. Chem. Hoppe–Seyler, 374*, Abstract No. PL 38, p. 532, (1993).
M R Pollard, et al., "A Specific Acyl–ACP Thioesterase Implicated in Medium–Chain Fatty Acid Production in Immature Cotyledons of *Umbellularia californica*", *Archives Biochem. Biophys., 284*, 306–312, (1991).
R Schuch, et al., *Fett Wissenschaft Technologie, 93*, 417, (Nov. 1991).
R Topfer, et al., "Molecular Cloning of cDNAs or Genes Encoding Proteins Involved in de novo Fatty Acid Biosynthesis in Plants", *J. Plant Physiology, 143*, 416–425, (1994).
T A Voelker, et al., "Fatty Acid Biosynthesis Redirected to Medium Chains in Transgenic Oilseed Plants", *Science, 257*, 72–74, (Jul., 1992).
Stam M, et al. "The silence of genes in transgenic plants." Ann. Bot. 79:3–12, 1997.
Koziel MG, et al. "Optimizing expression of transgenes with an emphasis on post–transcriptional events." Plant Mol. Biol. 32: 393–405, 1996.
Smith CJS, et al. "Antisense RNA inhibition of polygalacturonase gene expression in transgenic tomatoes." Nature 334: 724–726, Aug. 25, 1988.

*Primary Examiner*—Douglas W. Robinson
*Assistant Examiner*—Amy J. Nelson
*Attorney, Agent, or Firm*—Schwegman, Lundberg, Woessner & Kluth, P.A.

[57] ABSTRACT

The present invention is directed to DNA sequences that from *Cuphea lanceolata* code for a middle chain-specific acyl-[ACP]-thioesterase, and alleles and derivatives of these DNA sequences. The present invention also is directed to process for producing plants, parts of plants or plant products that contain these DNA sequences, alleles or derivative of these DNA sequences, where the plants, parts of plants or plant products produce fatty acids of middle chain length.

18 Claims, 8 Drawing Sheets

Acyl[ACP]-Thioesterase

5' Primer Number 3532 (SEQ ID NO:9)

```
    W    N    D    L    D    V    N    Q
5'  TGG  AAC  GAC  CTI  GAC  GTI  AAC  GA
         T    T    T         T         T
```

3' Primer Number 2740 (SEQ ID NO:10)

```
3'  T₁₈ CGAAGGATCCAAGCTTGTCGACT
```

FIG. 1

```
                1                                                          50
Ctte2_1  NO:13  ..........  ..........  ..........  ......ML  SRPLPTTAAA  ATTTTNNCNG
Ctte5_2  NO:14  ..........  ..........  ..........  ......ML  SKGAP..AAP  AVAAMYNASA
Bnte2    NO:11  ..........  ..........  ..........  ..........  ..........  ..MLKLSCNV
Clte13   NO:1   MVATAASSAF  FPLPSPDTSS  RPGKLGNGSS  SLS.PLKPKF  VANAGLKVKA
Clteg7   NO:6   MVATAASSAF  FPLPSPDTSS  RPGKLGNGSS  SLS.PLKPKF  VANAGLKVKA
Clte5    NO:2   ..........  ..........  ..........  ....LKPKS   IPNGGLQVKA
Clte4    NO:5   MVATAASSAF  FPVPSADTSS  RPGKLGNPS   SFS.PLKPKS  IPNGGLQVKA
Clteg16  NO:7   MVAAAASSAF  FSFPTPGTSP  KPGKFGNWPS  SLSVPFNLKS  NHNGGFQVKA
Pcr42    NO:8   ..........  ..........  ..........  ..........  ..........
Clte12   NO:3   ..........  ..........  ..........  ..........  ..........
Clteg1   NO:4   MVAAAATSAF  FPVPAPGTSP  KPGKSGNWPS  SLSPTFKPKS  IPNAGFQVKA
Ucte     NO:12  ..........  ..........  ...MATTSLA  SAFCSMKAVM  LARDGRGMKP
```

FIG. 3

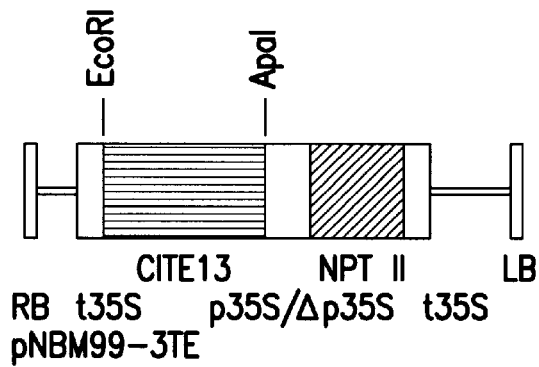
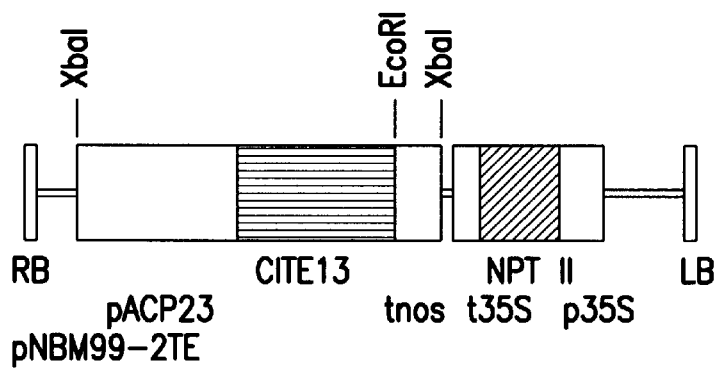
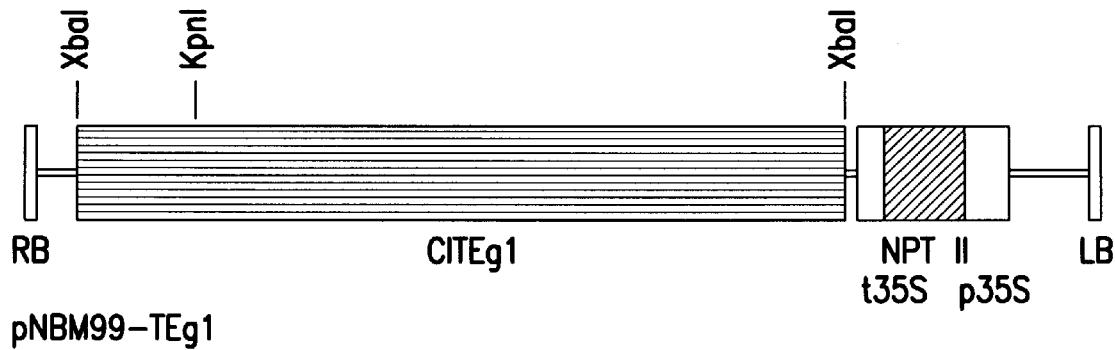
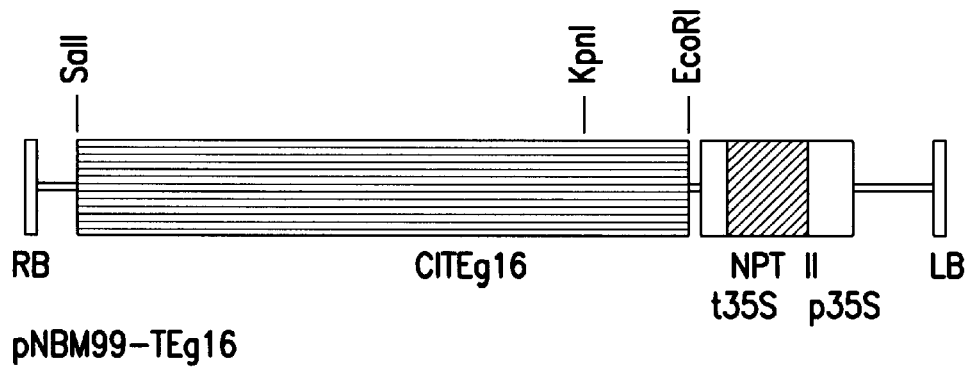
FIG. 4

MIDDLE CHAIN-SPECIFIC THIOESTERASE GENES FROM *CUPHEA LANCEOLATA*

FIELD OF THE INVENTION

This invention concerns DNA sequences which code for a middle chain-specific acyl-[ACP]-thioesterase, as well as alleles and derivatives of these DNA sequences.

BACKGROUND OF THE INVENTION

The thioesterases are substantially involved in the production of fatty acids in plant organisms. With respect to compartments the fatty acid and triacylglyceride biosynthesis can be viewed as separate biosynthesis. In view of the end product, they can be viewed as a single biosynthetic pathway. De novo biosyntheses of fatty acids is taking place in the plastids and is catalyzed by three enzymes or enzyme systems respectively, acetyl-coA Carboxylase (ACCase), the fatty acid synthase (FAS), and the acyl-[ACP]-thioesterase (TE).

In most organisms the end products of these reactive pathways are either palmitic acid ($C_{16:0}$), stearic acid ($C_{18:0}$) and, after desaturation oleic acid ($\Delta 9 C_{18:1}$). The acyl-[ACP]-thioesterase (TE) flnctions in the determination of the length of the chain.

In contrast, triacylglyceride biosynthesis takes places at the endoplasmic reticulum in the cytoplasm via the so-called "Kennedy Pathway" from glycerin-3-phosphate, which is probably provided as a result of the activity of glycerin-3-phosphate dehydrogenase (G3P-DH), and fatty acids, which occur as acyl-coA substrates.

In animal systems (e.g. the rat), the acyl-[ACP]-thioesterase is an integral part of the FASI and is responsible for the termination of the fatty acid biosynthesis there. A second acyl-[ACP]-thioesterase (TEII), which is expressed in specific tissues, is responsible for the early termination of chain elongation in the milk producing glands of the rat breast, and causes the release of $C_{10:0}$ and $C_{12:0}$ fatty acids. Expression of this TEII in mouse fibroblasts resulted in the formation of these middle chain fatty acids in these cells. It is therefore concluded, that this enzyme is significantly involved in the termination of chain length. (S. A. Bayley et al., Bio/Technology 6, p. 1219–1221 (1988)).

Acyl-[ACP]-thioesterases were also purified from plants, and analyzed for their activity. Acyl-[ACP]-thioesterases with preference for the hydrolysis of long chain acyl-[ACP] compounds were isolated from *Carthamus tinctorius* (T. A. McKeon et al., J. Biol. Chem. 257, p. 12141–12147 (1982)), *Cucurbita moschata* (H. Imai et al., Plant Mol. Biol. 20, p. 199–206 (1992)), and *Brassica napus* (A. Hellyer et al., Plant Mol. Biol. 20, p. 763–780 (1992)). Corresponding cDNAs have been isolated already from *Carthamus tinctorius* (D. S. Knutzon et al., Plant Physiol. 100, p. 1751–1758 (1992)) and *Brassica napus* (E. S. Loader et al., Plant Mol. Biol. 23, p. 769–778 (1993)). Another TE with specificity for the hydrolysis of $C_{12:0}$-[ACP] has been isolated from *Umbellularia Californica* (California Laurel), and was separated from the activity of a $C_{18:0}$-[ACP] specific TE (M. R. Pollard et al., Art. Biochem. Biophys. 284, p. 306–312 (1991)). In *Cuphea lanceolata*, the activity of a middle and a long chain-specific TE were detected as well (P. Dormann et al., Planta 189, p. 425–432 (1993)).

An only partially purified enzyme preparation of a $C_{10:0}$ specific acyl-[ACP]-thioesterase from *Cuphea hookeriana* is described in WO 91/16421. As measurements of the hydrolysis activities of the enzyme shows against various substrates, it contains significant amounts of activity which are not C10:0 specific.

For the TE from *Umbellularia Californica* a cDNA was isolated which codes for a middle chain-specific acyl-[ACP]-thioesterase. This TE caused the formation of middle chain fatty acids in seeds of transgenic Arabidopsis thaliana and *B. napus* plants, in particular lauric acid (C12:0) and in small amounts myristic acid (C14:0); (T. A. Voelker et al., Science 257, p. 72–74 (1992) and H. M. Davies and T. A. Voelker in Murata, N. and C. Somerville (editors): Current Topics in Plant Physiology: Biochemistry and Molecular Biology of Membrane and Storage Lipids of Plants, Vol 9, p. 133–137; American Society of Plant Physiologists, Rockville (1993)).

There is an increasing demand on the supply of middle chain fatty acids, e.g. capric acid ($C_{10:0}$), which can be used in industry as softeners, lubricants, pesticides, tensides, cosmetics, etc. One possibility to make these fatty acids available is in the isolation (extraction) of fatty acids from plants which show especially high contents of these fatty acids. The increase of content of middle chain fatty acids was achieved only to a limited extent by the classic method, which is the breeding of plants which produce elevated levels of these fatty acids.

Therefore it is the goal of this invention to provide genes or DNA sequences, which can be used to improve the yield of oils and the production of middle chain fatty acids in plants, which are not capable of producing these fatty acids themselves or only in small amounts.

SUMMARY OF THE INVENTION

This goal is achieved with the DNA sequences according to patent claim 1 or the genes from the genomic clones according to patent claim 6.

This invention concerns DNA sequences which code for a middle chain-specific acyl-[ACP]-thioesterase, and the alleles and derivatives of these DNA sequences.

Furthermore this invention concerns genomic clones, the DNA sequences which code for a middle chain-specific acyl-[ACP]-thioesterase and which contain promoters and regulatory sequences, and the alleles as well as the derivatives of these DNA sequences.

Furthermore, this invention concerns a process for the production of plants, parts of plants, and plant products, in which a DNA sequence, which codes for a middle chain-specific acyl-[ACP]-thioesterase, is transferred by means of gene technology.

Finally, this invention concerns the use of this DNA sequence for the transfer of genes for middle chain-specific acyl-[ACP]-thioesterases in plants.

SUMMARY OF THE FIGURES

The figures serve to explain the invention presented here. It is shown by:

FIG. 1 the presentation of the DNA and amino acid sequence of the degenerate oligonucleotides 3532 and 2740;

FIGS. 3A–3I a comparison of the amino acid sequences of thioesterases from various plants;

FIG. 4 functional parts of binary vectors for the expression of the claimed DNA sequences and genes from the genomic clones in transgenic plants;

DETAILED DESCRIPTION OF THE INVENTION

Figure 2:
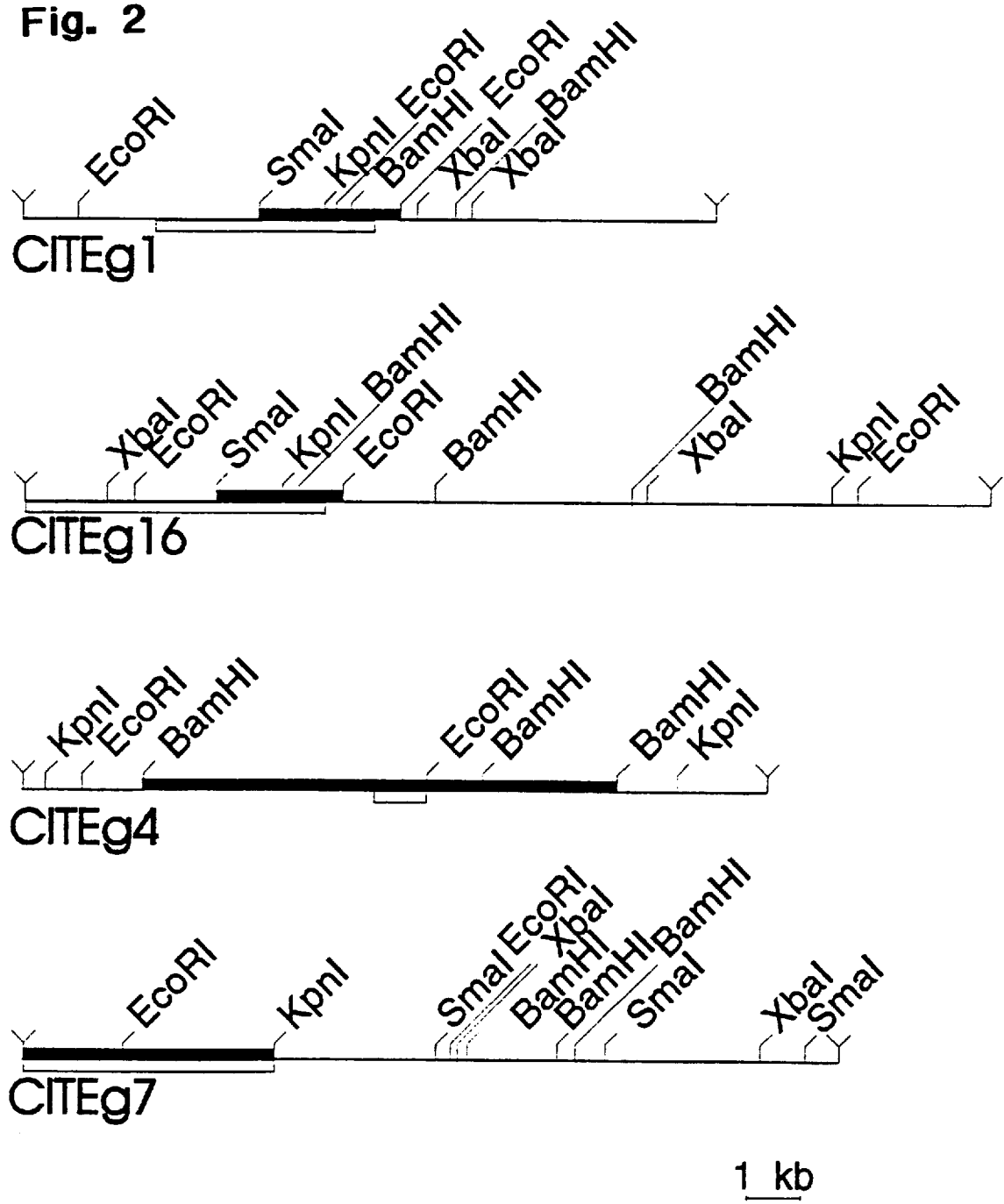
FIG. 2 the restriction maps of the genomic clones for the acyl-[ACP]-thioesterase ClTEg1, ClTEg16, ClTEg4 and ClTEg7 from *Cuphea lanceolata*.

It is self-evident, that allelic variants and derivatives of the DNA sequences, which are in accordance with the patent, are included in the scope of the invention, under the condition, that these modified DNA sequences and genes code for middle chain-specific acyl-[ACP]-thioesterases. For instance, deletions, substitutions, insertions, inversions or additions of the DNA sequences, which are in accordance with this invention, are considered to be allelic variants and derivatives.

The DNA sequences which are in accordance with this invention, as well as the genes from the genomic clones code for middle chain-specific acyl-[ACP]-thioesterases, which catalyze the formation of $C_{8:0}$ to $C_{14:0}$ fatty acids. In particular the invention applies to $C_{10:0}$ specific acyl-[ACP]-thioesterases or for the most part $C_{10:0}$ specific acyl-[ACP]-thioesterases and $C_{14:0}$ specific acyl-[ACP]-thioesterases or for the most part $C_{14:0}$ specific acyl-[ACP]-thioesterases, which are responsible for the formation of capric acid and myristic acid in fatty acid synthesis.

Any plant material, which produces these thioesterases in sufficient amounts, is suitable as the starting material for the isolation of genes which code for middle chain-specific acyl-[ACP]-thioesterases. The plant Cuphea lanceolata, which originates in Central America, has proven to to be an especially suitable starting material in the invention disclosed here. The seeds of this plant contain 83% capric acid.

In order to isolate DNA sequences in accordance with the patent, a cDNA library from Cuphea lanceolata (wild type) was searched for genes for middle chain-specific acyl-[ACP]-thioesterases with a hybridization probe, PCR42, which was obtained by PCR (Polymerase Chain Reaction). In this way, the cDNA-clones CITE13, CITE5 and CITE12 were isolated.

The thus obtained cDNAs were fully sequenced in both directions in the usual way. The CITE13-cDNA contains 1494 bp as an ApaI-EcoRI fragment, and contains the total structural gene for a middle chain-specific acyl-[ACP]-thioesterases. The CITE13-cDNA codes for a protein with 414 amino acids, which includes a deduced transit peptide of 111 amino acids. The full DNA sequence of the 1494 bp cDNA-fragment with the deduced amino acid sequence is presented as SEQ ID NO: 1 in the sequence listing. The coding region stretches from position 83 to position 1324 of the DNA sequence. The open reading frame begins at position 83 with the start codon "ATG", which codes for methionine, and ends at position 1324 with the stop codon "TAG". The deduced molecular weight of the mature protein is 34 kDa.

The DNA sequence analysis of the two other cDNAs CITE5 and CITE12 has shown that these do not contain the total structural gene for a middle chain-specific acyl-[ACP]-thioesterase. The DNA sequences of the named cDNAs, including the deduced amino acid sequences, are listed in the sequence listing as SEQ ID NO:2 and SEQ ID NO:3. The CITE5-cDNA has a length of 1404 bp as an EcoRI-XhoI-fragment and codes in the open reading frame for a protein with 375 amino acids, in which 34 amino acids of the transit peptide are missing relative to the deduced amino acid sequence of CITE13. The CITE12-cDNA has a length of 1066 bp as an EcoRI-XhoI-fragment, where the XhoI site is situated at the end, and codes according to the open reading frame for a protein of 287 amino acids, in which 20 amino acids of the mature protein and the transit peptide are missing.

In the following Table I the level of homology or identity is given between the acyl-[ACP]-thioesterase amino acid sequences of mature proteins of the CITE5 and CITE13 cDNAs (deduced from the DNA sequence) from Cuphea lanceolata, CtTE2-1 and CtTE5-2 from Carthamus tinctorius, and UcTE from Umbellularia californica.

TABLE I

|  | Percent Identity | | | | |
| --- | --- | --- | --- | --- | --- |
|  | CITE5 | CITE13 | CtTE2-1 | CtTE5-2 | UcTE |
| CITE5 |  | 91.3% | 44.8% | 48.2% | 57.0% |
| CITE13 | 96.0% |  | 44.2% | 45.7% | 57.9% |
| CtTE2-1 | 67.1% | 67.6% |  | 82.5% | 39.7% |
| CtTE5-2 | 71.1% | 69.5% | 91.1% |  | 41.6% |
| UcTE | 75.1% | 76.3% | 63.8% | 62.7% |  |
|  | Percent Homology | | | | |

The comparison of the TE amino acid sequence from CITE 13 with the thioesterase from U. californica (UcTE) shows a rather high agreement at 57.9% identical amino acids, which is higher than the agreement to the long chain-specific thioesterases from C.tinctorius (CtTE-2-1 and CtTE5-2). The thioesterase of CITE5 shows a rather high agreement with UcTE at 57.0% identity.

FIG. 3 shows an amino acid sequence comparison between thioesterases from plants. The sequences of the mature proteins (exception: CITE12, —20 amino acids) are deduced from the corresponding thioesterase (TE) cDNAs from Carthamus tinctorius=Ct, Cuphea lanceolata=Cl, Brassica napus=Bn and Umbellularia californica=Uc. PCR42 is the PCR product that was used in the screening of the cDNA libraries. The gap between positions 374 and 393 (ca. 20 amino acids) occurs only in the middle chain-specific thioesterases, and is close before the sole cysteine (position 359) which is conserved throughout all the sequences, which is presumed to be the active cysteine residue. By changing the subsequence between the named positions and others, see below, the chain length specificity of thioesterases can be influenced through genetic engineering.

Furthermore, genomic clones were isolated and characterized from Cuphea lanceolata, which contain the full-length structural gene of a middle chain-specific acyl-[ACP]-thioesterases including regulatory sequences (as promoters and terminators). This means that they form fully functional transcriptional units. During screening of a genomic library from Cuphea lanceolata with CITE5-cDNA as a probe, 23 genomic clones were isolated. The genomic clones CITEg1, CITEg16, CITEg4, and CITEg7 are shown in FIG. 2 and characterized by restriction analysis with various restriction enzymes. The DNA-fragments in question show a size of 12.7 kb for CITEg1, 17.4 kb for CITEg16, 13.5 kb for CITEg4 and 14.7 kb for CITEg7. The restriction mapping has concluded that the shown genomic clones belong to four different classes of genes. It was determined from sequencing data, that the cDNA CITE5 corresponds to the gene of the genomic clone ClTEg4, the ClTE12-cDNA the gene of the genomic clone ClTEg1, the ClTE13-cDNA the gene of the genomic clone ClTEg7, and the PCR product PCR42 to the gene from the genomic clone ClTEg16.

Internal sequence primers, positioned at the 5'-end, were deduced from the cDNA sequences described above. These primers were used to obtain sequence data from the genomic clones, which give information about the start of the coding region and also about the limits of the promoters of the thioesterase gene. As a result of these diagnostic sequence regions of the genomic clones ClTEg1, ClTEg16, ClTEg4 and ClTEg7 in the area of the smallest hybridizing fragments (see black bar in FIG. 2), it was possible to establish apart from the identity as genes for middle chain-specific thioesterases in comparison with the amino acid sequence of *U.californica* thioesterase, also the completeness of the thioesterase gene as transcriptional units.

The thioesterase genes were identified by DNA sequence analysis of selected sequence fragments of the genomic clones ClTEg1, ClTEg4, ClTEg7, and ClTEg16. The sequenced regions are recognizable as white bars under the clones shown in FIG. 2. All genes consist of seven exons, where the first exon is not in the area of the mRNA that is translated. The structural gene of a middle chain-specific acyl-[ACP]-thioesterase is located on a 4098 bp DNA-fragment of clone ClTEg1, see SEQ ID NO:4 in the sequence listing. The coding region starts with exon II at position 1787 and ends with exon VII at position 3941. A 4643 bp DNA-fragment of the clone ClTEg7 contains the structural gene of a middle chain-specific acyl-[ACP]-thioesterase. As can be seen from SEQ ID NO:6 in the sequence listing, the coding region begins at position 773 with exon II and ends with exon VII at position 3118. The genomic clone ClTEg16 contains the structural gene for a middle chain-specific acyl-[ACP]-thioesterase on a 5467 bp DNA-fragment. See SEQ ID NO:7 in the sequence listing. The coding region begins with exon II at position 3284 and ends with exon VII at position 5275. The coding region for the structural gene of a middle chain-specific acyl-[ACP]-thioesterase is incomplete for genomic clone ClTEg4. SEQ ID NO:5 in the sequence protocol shows exon II at positions 1 through 502 as well as the incomplete intron II at positions 503 through 928 on a 928 bp DNA fragment.

The structural genes for the middle chain-specific acyl-[ACP]-thioesterases, which were detected in the genomic clones ClTEg1, ClTEg7, and ClTEg16, each contain seven exons of almost identical size. Exon II of the thioesterase from clone ClTEg4 falls into the same order of size as the exons II of the other thioesterases. It is possible that intron I of all genes is responsible for regulatory functions in gene expression.

The genomic clone ClTEg4 was deposited under number DSM 8493, and the genomic clone ClTEg7 under the number DSM 8494, on Aug. 27, 1993 at the DSM-Deutsche Sammlung von Mikroorganismen und Zellkulturen GmbH (DSM—German Collection of Microorganisms and Cell Cultures, Inc.), Mascheroder Weg 1B, D-38124 Braunschweig.

The DNA sequences, which are in accordance with the patent, which code for a middle chain-specific acyl-[ACP]-thioesterase, can be introduced/transferred into plants by application of gene technological procedures, and can lead to production of these fatty acids in these plants (in the form of anti-sense or over expression). The DNA sequences, which are in accordance with the patent, are introduced into plants in particular with recombinant vectors, for instance binary vectors, preferably together with suitable promoters, unless they consist as complete transcriptional units.

The genomic clones ClTEg1, ClTEg16, ClTEg4 and ClTEg7 can be used as self-complete transcriptional units (which contain promotor, structural gene, and teminator) for the transformation of plants, whereby middle chain-specific fatty acids are accumulated in the storage lipids. The yield of middle chain fatty acids can be optimized by crossings and the resultant combination of thioesterase genes. An optimization can take place by increasing the content of newly introduced fatty acids, or by production of various new fatty acids.

All varieties of plants can be transformed for this purpose. Preferably, such plants are being transformed, which are supposed to show an increased production of middle chain-specific fatty acids, and such plants as do not naturally synthesize these fatty acids. In this context oil plants, for instance rapeseed, sunflower, flax, oil palm and soybean are to be named.

The gene technological introduction of DNA sequences, which are in accordance with the patent, which code for acyl-[ACP]-thioesterase, can be made with the aid of the usual transformation techniques. Such techniques include procedures like direct gene transfer, for instance micro injection, electroporation, particle gun, the soaking of parts of plants in DNA solutions, pollen or pollen tube transformation, viral vectors and liposome-facilitated transfer, as well as the transmission of the appropriate recombinant Ti-plasmids or Ri-plasmids with Agrobacterium tumefaciens and the transformation with plant viruses.

In the present invention, the ClTE13-cDNA was first introduced into the binary vector pRE9 (pNBM99-3TE) as an ApaI-EcoRI fragment behind a double promotor constructed from 35S RNA from Cauliflower Mosaic Virus (p35S/ΔP35S), second the same fragment was introduced in the binary vector pRE1 (pNBM99-2TE), behind the seed specific ACP23-promotor from rapeseed. Furthermore, a XbaI-fragment (7.3 kb) from the genomic clone ClTEg1 and a SalI-EcoRI-fragment (6 kb) from the genomic clone ClTEg16 were introduced into pRE1. The resulting binary vectors are pNBM99-TEg1 and pNBM99-TEg16. The TE gene from ClTEg1 is in 3'-5' orientation in pRE 1, and the gene from ClTEg16 in 5'-3' orientation. The functional parts of the thus obtained expression vectors are shown in FIG. 4.

The abbreviations used in FIG. 4 have the following meaning:
RB and LB=right and left border of the transfer DNA
pACP23=promotor of the Acyl-carrier-protein gene 23 from rape
ClTE13=CDNA 13 from *Cuphea lanceolata*
tnos=terminator of the Nopalinsynthase gene from Agrobacterium tumefaciens
NPTII=Neomycinphosphotransferase gene II
p35S=promotor of the 35S RNA of the cauliflower mosaic virus
t35S=ten-ninator of the 35S RNA of the cauliflower mosaic virus
35S=minimal promotor of the 35S RNA of the cauliflower mosaic virus The middle chain specificity of cDNA, which is in accordance with the patent, as well as the genes from the genomic clones, was analyzed by transformation. Appropriate plant materials are, for instance, rape and tobacco, since these plants are capable of producing only longer chain fatty acids, starting at C16:0 and up.

To this purpose the expression vectors pNBM99-TEg1 and pNBM99-TEg16 were transformed, independently of each other, into rape through Agrobacterium. On Aug. 27, 1993 the expression vector pNBM-TEg1 was deposited with the DSM (Deutsche Sammlung von Mikroorganismen und Zellkulturen GmbH, Mascheroder Weg 1B, D-38124 Braunschweig) under number DSM 8477, and the expression vector pNBM99-TEg16 under number DSM 8478.

Independent of each other, the expression vectors pNBM99-2TE and pNBM99-3TE were transformed into tobacco with Agrobacterium tumefaciens.

Figure 5:
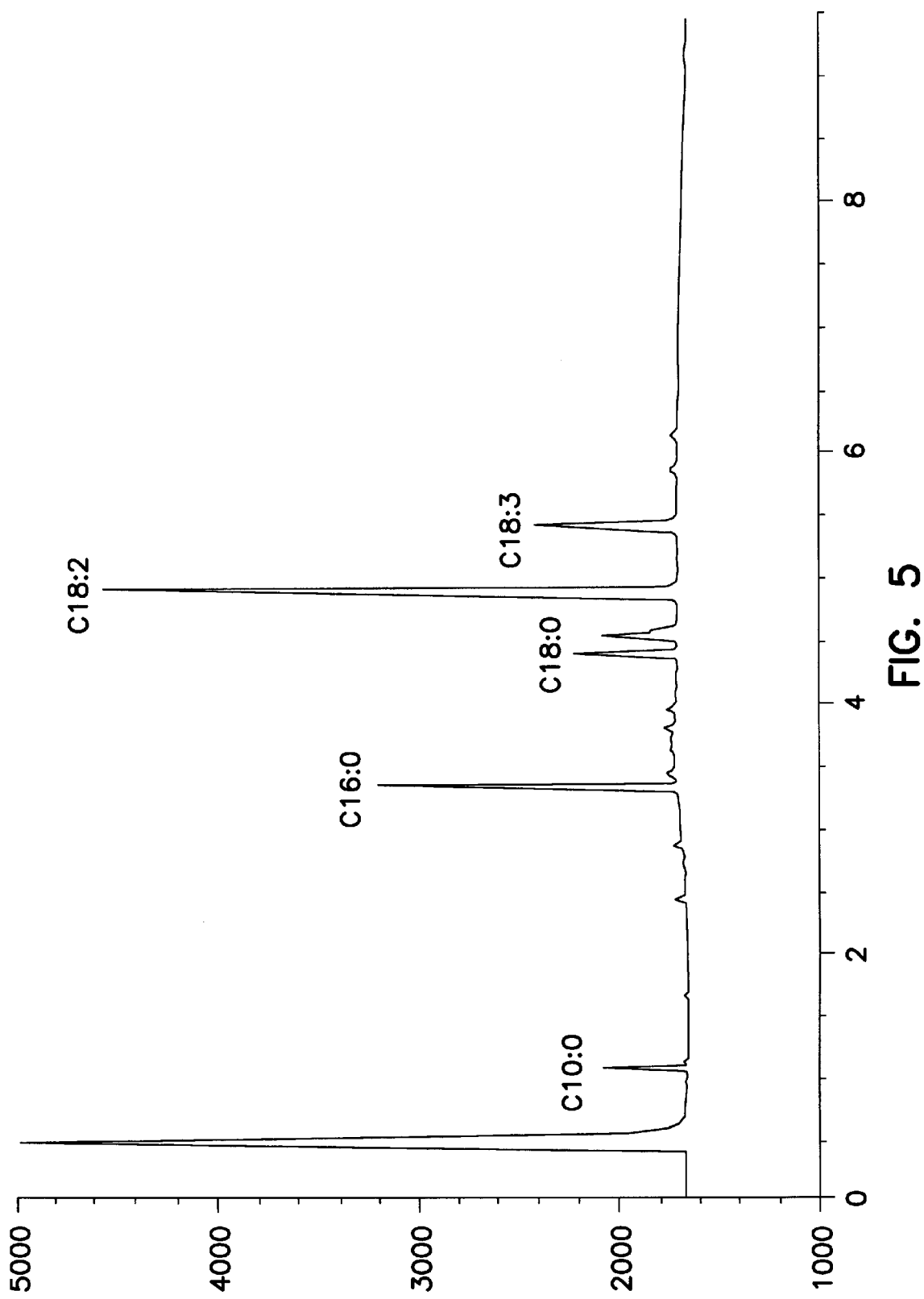
FIG. 5 the gas chromatogram of the contents of fatty acids in unripe rape seeds (pNBM99-2TE)
Figure 6:
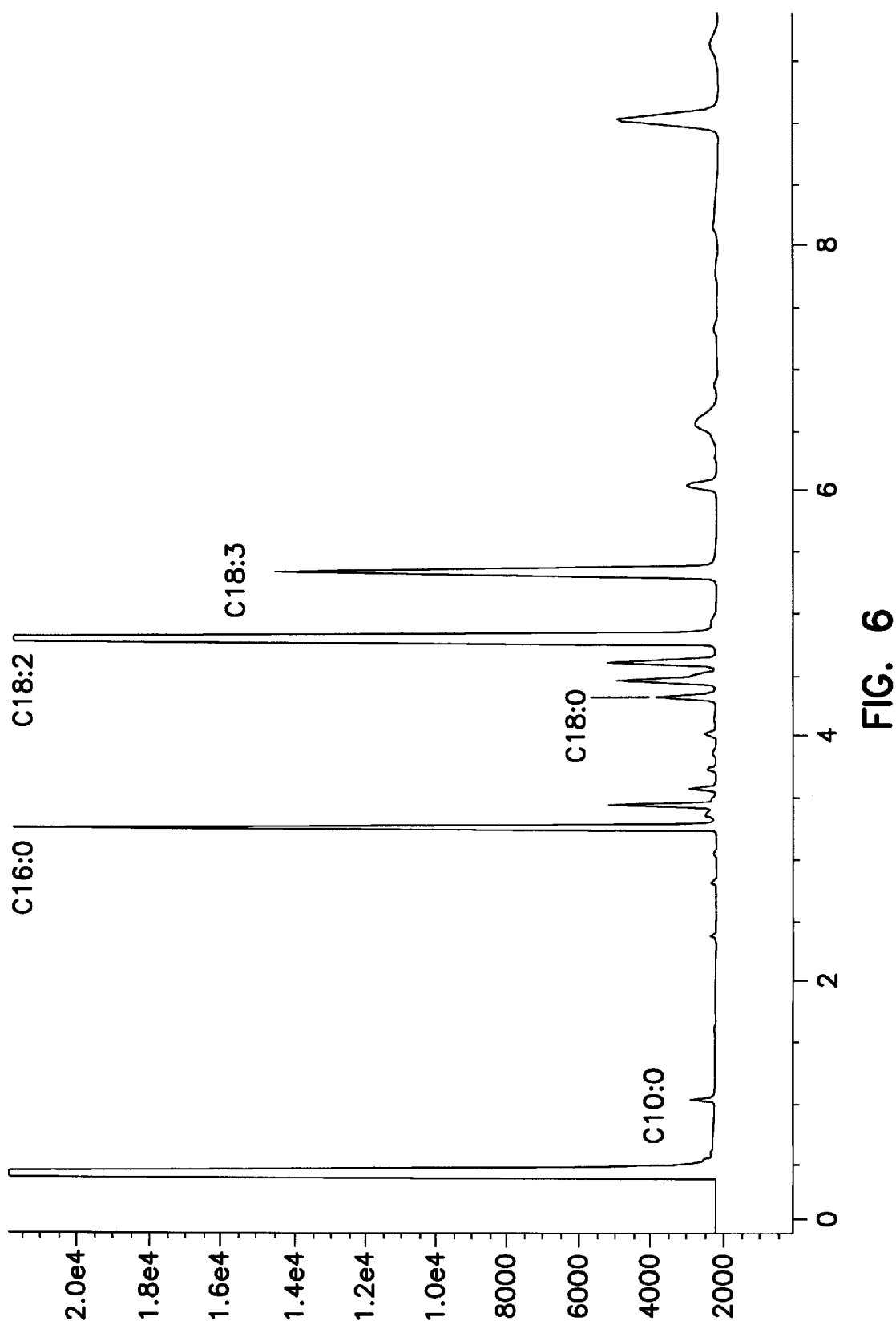
FIG. 6 the gas chromatogram of the contents of fatty acids in unripe tobacco seeds (pNBM99-2TE)

Then the transformed rape and tobacco plants were analyzed for their content of middle chain fatty acids. For this purpose, ripening seeds were analyzed by gas chromatography. FIGS. 5 and 6 show gas chromatograms from fatty acid extracts from transgenic rape and tobacco seeds, which had been transformed with the pNBM99-2TE construct.

As can be seen on the gas chromatograms, transgenic rape as well as transgenic tobacco are producing capric acid ($C_{10:0}$). Therefore it can be concluded that the cDNA ClTE13 and the gene from the genomic clone ClTEg7 (see above) code for a thioesterase, which is specific for $C_{10:0}$ or for the most part specific for $C_{10:0}$.

Figure 7:
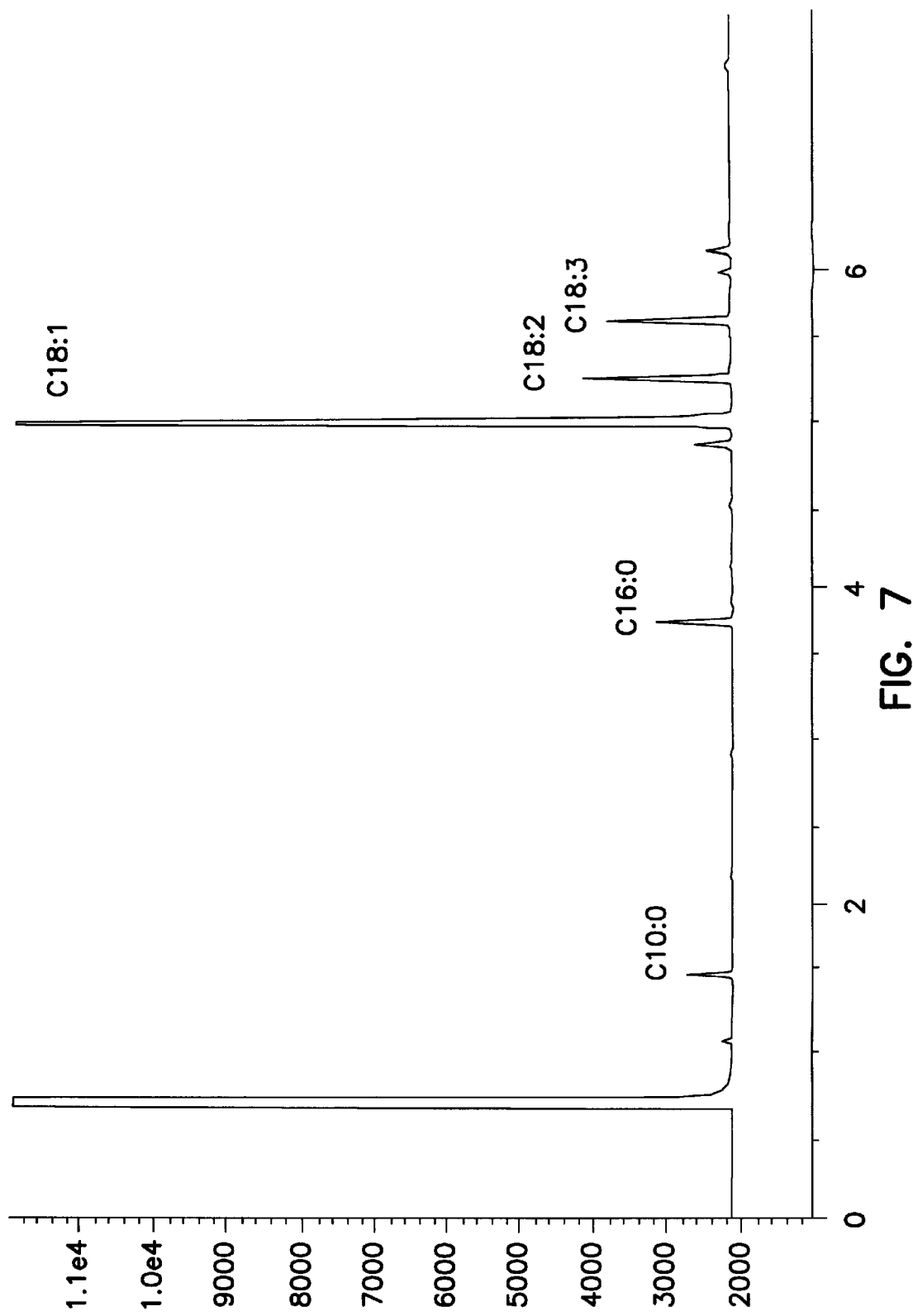
FIG. 7 the gas chromatogram of the contents of fatty acids in ripe raps seeds (pNBM99-TEg1)
Figure 8:
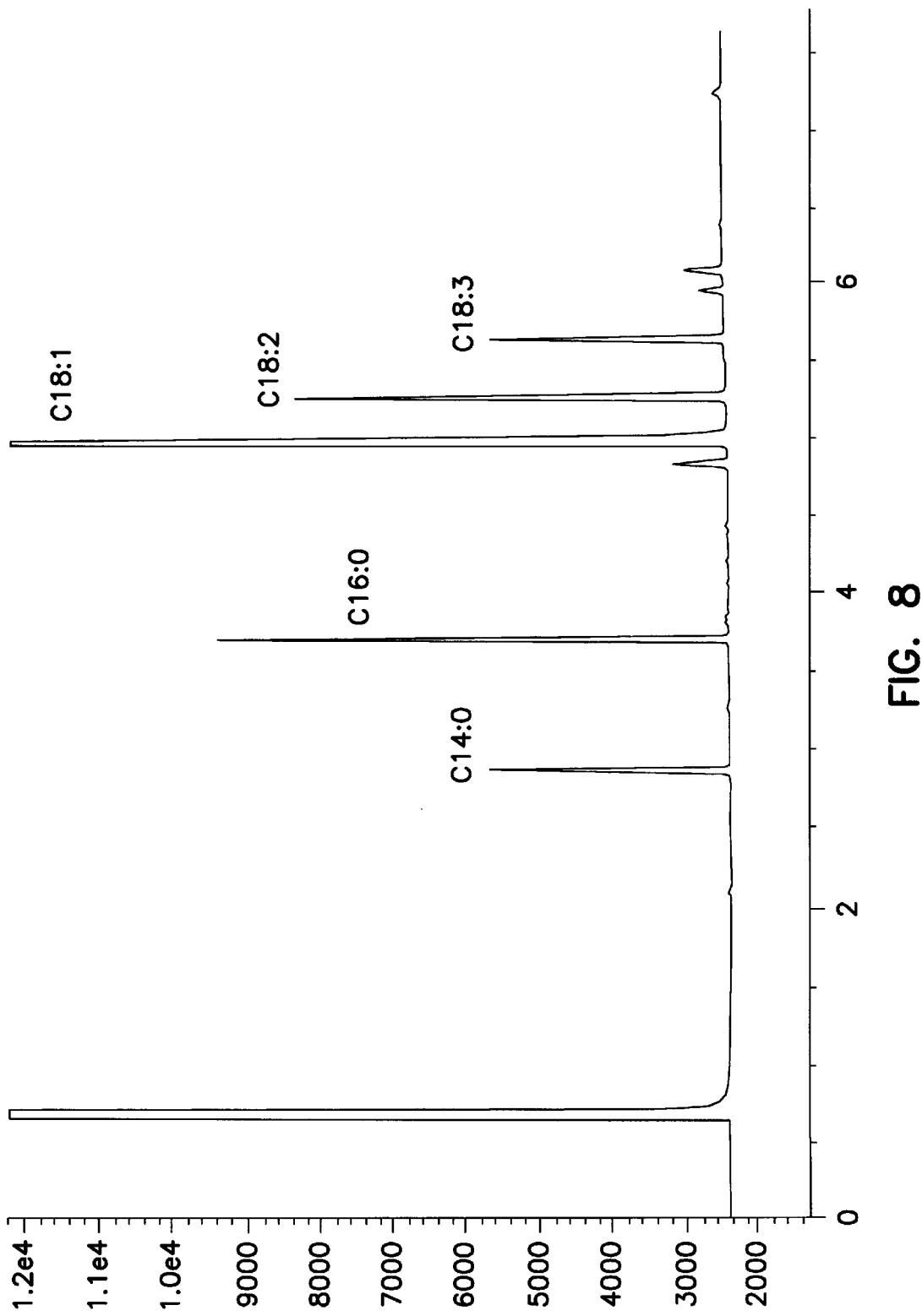
FIG. 8 the gas chromatogram of the contents of fatty acids in ripe rape seeds (pNBM99-TEg16).

It was determined in further studies on transgenic ripe rapeseeds, which were transformed with the expression vectors pNBM99-TEg1 and pNBM99-TEg16, that in the gas chromatograms of the fatty acid extracts the following amounts are produced: in the case of the gene from the genomic clone ClTEg1 (FIG. 7) 1.7% capric acid ($C_{10:0}$) and 0.4% caprylic acid ($C_{8:0}$), and in the case of the gene from the genomic clone ClTEg16 (FIG. 8) 5.4% myristic acid ($C_{14:0}$). The following table II shows the change in the fatty acid patterns of the transgenic rape plants in this study. The values refer to the %–fraction of fatty acid in ripe seed.

that the cDNA, which is in accordance with this invention, as well as the genes from the disclosed genomic clones do not cause problems with tolerance in rape and tobacco. The proper compartmentalization is insured because of the available transit peptide. For the regulated expression of the ClTE13-cDNA it is possible to use a seed specific expressing promotor, and the genes from the shown genomic clones are themselves regulated by their own tissue specific promoters. Position effects can be balanced out by the necessary number of tranformants.

Therefore, the DNA sequences, which are in accordance with this invention, in form of the disclosed cDNAs as well as in form of the isolated genes from the shown genomic clones, are appropriate for the production of middle chain specific fatty acids in transgenic plants, preferably oil plants. An optimization of the content of middle chain specific fatty acids can be accomplished by additional transfer into rape of components of the fatty acid synthase systems, e.g. DNA sequences for ACP2, a specific KAS, keto reductase and enoyl reductase, for instance from *Cuphea lanceolata*. Over and above that it can be expected that the LPA-AT (lysophosphatide-acyl-transferase), e.g. from *Cuphea lanceolata*, which is located in the cytoplasm, can cause a marked increase in the content of middle chain fatty acids in the triacylglycerides in rape.

The following examples serve the explanation of this invention.

EXAMPLES

The plant material, which was used in the frame of the presented invention, consisted of the varieties *Brassica napus* (Cruciferae) (rape), *Nicotiana tabacum* (Solanaceae) (tobacco), and *Cuphea lanceolata* (Lythraceae) (lancett leaved quiver flower). The summer rape line Drakkar and the tobacco line Petit Havanna SRI were used for transformation.

TABLE II

| Construct | $C_8$ | $C_{10}$ | $C_{12}$ | $C_{14}$ | $C_{16}$ | $C_{18:0}$ | $C_{18:1}$ | $C_{18:2}$ | $C_{18:3}$ | $C_{20:0}$ |
|---|---|---|---|---|---|---|---|---|---|---|
| Control | — | — | — | — | 3.0 | 2.3 | 76.5 | 9.9 | 6.0 | 0.8 |
| pNBM99-TEg1 | 0.4 | 1.7 | — | — | 3.4 | 2.2 | 75.4 | 8.2 | 6.5 | 0.8 |
| pNBM99-TEg16 | — | — | — | 5.4 | 13.4 | 1.9 | 56.6 | 13.7 | 7.1 | 0.7 |

It follows, that the gene on the genomic clone ClTEg1 and the cDNA ClTE12 (see above) code for a $C_{10:0}$ specific acyl-[ACP]-thioesterase or an for the most part $C_{10:0}$ specific acyl-[ACP]-thioesterase. The gene on the genomic clone ClTEg16 codes for a $C_{14:0}$ specific acyl-[ACP]-thioesterase or a for the most part $C_{14:0}$ specific acyl-[ACP]-thioesterase. On comparing the amino acid sequences in FIG. 3 it can be noticed that the C10/C14 difference of ClTEg1 and ClTEg16 can be attributed to minor sequence variations "RR" (positions 395/396) and "D" (position 398), etc. Furthermore there is a gap (five amino acids) and amino acid changes in the area of positions 127 through 135. These regions may influence the chain length limits.

The DNA sequences, which are in accordance with the patent, and the genes from the genomic clones isolated from *Cuphea lanceolata* are ideally suited to confer to transformed plants the capability to produce middle chain specific fatty acids. This means, that it is possible to confer a fully functional gene for a middle chain specific acyl-[ACP]-thioesterase. In gas chromatographic studies of transgenic rape and tobacco the formation of capric acid and myristic acid was proven by the transfer of genes for a $C_{10:0}$ or $C_{14:0}$ specific acyl-[ACP]-thioesterase, or an for the most part $C_{10:0}$ or $C_{14:0}$ specific acyl-[ACP]-thioesterase. It turned out Example 1
Production of cDNAs of Acyl-[ACP]-Thioesterase from *Cuphea Lanceolata*

First a cDNA library was constructed from *Cuphea lanceolata* (wild-type). This cDNA library was constructed according to the specifications of the producer (Stratagene) with the help of the cDNA ZAP-synthesis kit. As starting material for the synthesis of the cDNAs served polyA+–mRNA from isolated two to three week old immature embryos. The thus obtained cDNA library has a size of 9.6×105 recombinant phages with a fraction of about 50% of clones, which contain insertions of more than 500 bp.

For the screening of the cDNA library described above, a specific hybridization probe was constructed for the acyl-[ACP]-thioesterase. In order to accomplish this, proper oligonucleotides are necessary. Voelker et al. (1992), Science 257, p. 72–74 describe the DNA sequence of a plant acyl-[ACP]-thioesterase. From a few areas of the sequence, which are as little degenerated as possible, oligonucleotide primers were deduced and synthesized. The primer 3532, which corresponds to the amino acids 277–284 of the acyl-[ACP]-thioesterase from *Umbellularia californica*, is appropriate for amplification of a specific hybridization probe in PCR reactions in conjunction with the primer 2740

(a modified oligo-dT-primer with restriction sites for the enzymes BstBI, BarnHI, HindIII, and SalI).

FIG. 1 and SEQ ID NO:9 and SEQ ID NO:10 in the sequence listing show the sequences of the synthetic oligonucleotides primers 3532 and 2740, which were used for the PCR reaction. The orientation of the oligonucleotide primers is from 5' to 3' for primer 3532, and 3' to 5' for the primer 2740.

A cDNA synthesis was carried out at 37° C. for 30 minutes, starting with 1 ug poly A+-RNA with reverse transcriptase (Boehringer Mannheim GmbH) from Avian Myeloblastosis Virus (AMV). To this purpose the 3'-oligonucleotide primer (2740), which is shown in FIG. 1, was used. After inactivation of the reverse transcriptase by heating for 5 minutes at a temperature of 95° C., the PCR reaction was carried out in the same sample with 50 pmol end concentration per primer and 4 units of Ampli-Taq-Polymerase (perkin Elmer Cetus). The reactions took place under the following conditions: a) buffer conditions: 10 mM Tris-HCl, pH=8.0; 50 mM KCl; 1.5 mM $MgCl_2$; 0.01% gelatine and 5 mM dNTPs, b) reaction time and temperatures: 3 minutes at 92° C. for first denaturation, then 25 to 30 temperature cycles with: 2 minutes at 92° C. for denaturation, 2 minutes at 50° C. for the annealing of the oligonucleotides, and 2.5 minutes at 72° C. for the amplification of the DNA, as well as a final 7 minutes at 72° C., to achieve complete synthesis of the last synthesis products.

The thus produced amplification products then were cloned. To this purpose, protruding ends of single-stranded DNA of the PCR products was filled in with Klenow-Polymerase, and subsequently phosphorylated with polynucleotide kinase (Sambrook et al., A Laboratory Manual, 2nd edn., (1989)).

The purification of the PCR products was performed according to standard protocols as described in Sambrook (see above) by agarose gel electrophoresis, gel elution, extraction with phenol/chloroform, and subsequent precipitation with isopropanol. The in this way obtained purified DNA was ligated into SmaI cleaved pBluescript-vector-DNA, and cloned.

Afterwards, the cloned PCR-fragment was sequenced by the method of Sanger et al. Proc. Natl. Acad. Sci. 74, p 5463–5467. The DNA sequencing took place partially radioactive by using the Sequencing-Kit, partially by using the Pharmacia Automated Laser Fluorescent A.L.F.—DNA Sequencing Automate. The sequences were analyzed with computer software of the University of Wisconsin Genetics Computer Group (Devereux et al., Nucl. Acids Res. 12, p. 387–395).

As can be seen from the sequence of the 530 bp acyl-[ACP]-thioesterase-PCR-product PCR42, which is shown as SEQ ID NO:8 in the sequence listing, a PCR product has been synthesized which shows significant homology to the starting sequence. The corresponding amino acid is shown below the DNA sequence.

The above described 530 bp PCR product was used as a probe for the isolation of acyl-[ACP]-thioesterase-cDNAs.

To this purpose the CDNA library described above was screened with the PCR product and 11 cDNAs were isolated, which could be attributed to three classes based on their sequences.

In this context, the cDNA clones ClTE13, CITE5, and ClTE12 were isolated, each of which represents one of the three classes. Their DNA sequences as well as the deduced amino acid sequences are presented as SEQ ID NO: 1, 2 and 3 in the sequence listing.

Example 2
Production of Genomic Clones of Acyl-[ACP]-Thioesterase from *Cuphea lanceolata*

To this purpose genomic DNA from young leaves from *Cuphea lanceolata* was isolated (S. L. Della Porta, J. Wood and J. B. Hicks, A plant DNA minipreparation: Version 11, Plant. Mol. Biol. Rep. 1, p 19–21 (1983)). Then the DNA was partially cleaved with the restriction enzyme Sau3A, after which the DNA fragments in the size range between 11000 bp and 19000 bp were cloned into the XhoI cleaved vector FIX II (Stratagene), which was done after the participating cleavage sites were partially filled each with two nucleotides. The non-amplified genomic DNA bank represented 5.4 times the genome of *Cuphea lanceolata*. From this bank, 102 hybridizing phages were isolated with ClTE5-cDNA as a probe. 40 of these were further purified and 23 were mapped. These allow themselves to be partitioned into four classes. Refer to FIG. 2, which shows the genomic clones ClTEg1, ClTEg16, ClTEg4 and ClTEg7, which can be attributed to different classes. Appropriate DNA-fragments of the genomic clones were sequenced. Their DNA sequences as well as the deduced amino acid sequences are presented as SEQ ID NO:4, 5, 6 and 7 in the sequence listing.

Example 3
Transformation of Rape and Tobacco

Appropriate expression vectors were constructed. To this purpose, a chimeric gene, consisting of the ClTE13-cDNA, the promotor ACP23 and the terminator tnos, was inserted into the binary vector pRE1. The resulting vector is pNBM99-2TE. The vector pNBM99-3TE was produced by introduction of the ClTE13-cDNA after the constructed double promotor of the 35S RNA from cauliflower mosaic virus (p35S/dp35S) into the binary vector pRE9. Further expression vectors were produced using the genomic clones ClTEg1 and ClTEg16 and the binary vector pRE I. The thus obtained expression vectors were designated pNBM99-TEg1 and pNBM99-TEg16.

The transformation of rape was carried out with Agrobacterium tumefaciens following the protocol of DeBlock et al., Plant Physiol. 91, p. 694–701, starting with hypocotyl pieces. The Agrobacterium strain GV3101 C58C 1 Rifr (Van Larebeke et al., Nature 252, p. 169–170 (1974)) was used with the Ti-plasmid pMP90RK (C. Koncz, J. Schell, Mol. Gen. Genet. 204, p. 383–396 (1986)) and the above named expression vectors. The selection for kanamycin resistance was carried out with 50 µg (Medium A5), later with 15 µg kanamycin (Monosulphate, Sigma K-4000) per milliliter medium (Medium A6 and A8). The transformation rate was 10%, with respect to the number of hypocotyl pieces that were laid out. This number is based on the verification of transformation by Southern-blot analysis (Sambrook et al., supra) and (PCR-Edwards et al., Nucl. Acids Res. 19, p. 1349 (1991)).

The transformation of tobacco was carried out with the above named vector system according to the "Leaf-disc" transformation procedure (R. B. Horsch et al., Pant (notice by translator: probably ought to be: Plant) Mol. Biol. 20, p. 1229–1231 (1985)).

The analysis of fatty acids in the transformed plants was carried out according to the method by W. Thies, Z. Pflanzenzuechtung 65, p. 181–202 (1971) and W. Thies, Proc. 4th Int. Rape Seed Con., 4.–8. June, Giessen, p. 275–282 (1974) with a Hewlett-Packard gas chromatograph (Model HP5890 Series II with FID) and a 10 m long capillary column (FS-FFAP-CB-0.25 from CS-Chromatographie-Service GmbH, Langerwehe). The separation of fatty acid methyl-esters took place in a temperature gradient from 140° C. to 208° C. with hydrogen as carrier gas, with a temperature rising at 20° C. per minute. After reaching the final temperature of 208° C., the separation proceeded isothermally for seven minutes. Injector and detector were held at a constant 250° C.

In any case, should a molecular biological procedure not have been adequately described, it was carried out following standard methods, as described by Sambrook et al., supra.

We claim:

1. An isolated nucleic acid that encodes the amino acid sequence encoded by the genomic DNA sequence of SEQ ID NO:5, SEQ ID NO:6, SEQ ID NO:4, or SEQ ID NO:7.

2. The isolated nucleic acid of claim 1, which comprises the genomic DNA sequence of SEQ ID NO:4.

3. The isolated nucleic acid of claim 1, which comprises the genomic DNA sequence of SEQ ID NO:7.

4. An isolated nucleic acid that encodes the amino acid sequence encoded by the cDNA sequence of SEQ ID NO:1, SEQ ID NO:2, or SEQ ID NO:3.

5. The isolated nucleic acid of claim 4, which comprises the cDNA sequence of SEQ ID NO:1.

6. The genomic clone ClTEg4 (DSM 8493) which comprises the nucleic acid sequence of SEQ ID NO:5.

7. The genomic clone ClTEg7 (DSM 8494) which comprises the nucleic acid sequence of SEQ ID NO:6.

8. The plasmid pNBM99-TEg1 (DSM 8477).

9. The plasmid pNBM99-TEg16 (DSM 8478).

10. A method of producing a transformed plant cell which comprises fatty acids of middle chain length, said method comprising the step of transferring by means of gene technology the isolated nucleic acid of claims 1 or claim 4 into a cell of a plant to form a transformed plant cell, wherein said isolated nucleic acid is expressed to yield said fatty acids.

11. The method of claim 10, wherein the plant cell comprises capric acid ($C_{10:0}$).

12. The method of claim 10, wherein the plant cell comprises myristic acid ($C_{14:0}$).

13. The method of claim 11, which further comprises transferring by means of gene technology an isolated nucleic acid which codes for acyl carrier protein 2 (ACP), ketoacyl-ACP-synthase (KAS), ketoreductase, enoylreductase, or lysophosphatide-acyltransferase.

14. The method of claim 12, which further comprises transferring by means of gene technology an isolated nucleic acid which codes for acyl carrier protein 2 (ACP), ketoacyl-ACP-synthase (KAS), ketoreductase, enoylreductase, or lysophosphatide-acyltransferase.

15. The method of claim 10 wherein the isolated nucleic acid is transferred by microinjection, electroporation, particle gun, the soaking of parts of plants in DNA solutions, pollen or pollen tube transformation, transfer of appropriate recombinant Ti-plasmids or Ri-plasmids from *Agrobacterium tumefaciens*, liposome-mediated transfer, or plant viruses.

16. The method of claim 10, further comprising the step of regenerating plants or plant parts from the transformed plant cell.

17. A plant cell produced by the procedure of claim 10.

18. Plants or plant parts produced by the procedure of claim 16.

* * * * *

```
                          SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 1494 Base pairs
        (B) TYPE: nucleic acid
        (C) STRANDEDNESS: double stranded
        (D) TOPOLOGY: linear (ii) MOLECULE TYPE:: c-DNA to m-RNA (iii) HYPOTHETICAL: No (iii) ANTI-SENSE: No (vi) ORIGINAL SOURCE:
         (A) ORGANISM: Cuphea lanceolata (vii) IMMEDIATE SOURCE:
          (A) LIBRARY: c-DNA Bank ZAP
          (B) CLONE: C1TE13

(ix) FEATURE:
         (A) NAME/KEY: CDS
         (B) LOCATION: 83..1324

(ix) FEATURE:
         (A) NAME/KEY: Transit-Peptide
         (B) LOCATION: 83..415

(ix) FEATURE:
         (A) NAME/KEY: mature Protein
         (B) LOCATION: 416..1324

(ix) FEATURE:
         (A) NAME/KEY: Startcodon
         (B) LOCATION: 83..85

(ix) FEATURE:
         (A) NAME/KEY: Stopcodon
         (B) LOCATION: 1325..1327

(xi) SEQUENCE DESCRIPTION: SEQ ID NO: 1:

GGGCCCCCTC GTGCCGCTCG TGCCGTTTTT TTGTCGCCAT TCGCCTCTCC TCTCCTCTCC        60

TCTCCTCTTC AGTTGGAAAA CA ATG GTG GCC ACC GCT GCA AGT TCT GCA TTC       112
                         Met Val Ala Thr Ala Ala Ser Ser Ala Phe
                          1               5                  10

TTC CCC CTG CCG TCC CCG GAC ACC TCC TCT AGG CCG GGA AAG CTC GGA        160
Phe Pro Leu Pro Ser Pro Asp Thr Ser Ser Arg Pro Gly Lys Leu Gly
                15                  20                  25

AAT GGG TCA TCG AGC TTG AGC CCC CTC AAG CCC AAA TTT GTC GCC AAT        208
Asn Gly Ser Ser Ser Leu Ser Pro Leu Lys Pro Lys Phe Val Ala Asn
         30                  35                  40
```

-continued

| | | | | | | | | | | | | | | | | |
|---|---|---|---|---|---|---|---|---|---|---|---|---|---|---|---|---|
| GCC | GGG | TTG | AAG | GTT | AAG | GCA | AGC | GCC | AGT | GCC | CCT | CCT | AAG | ATC | AAT | 256 |
| Ala | Gly | Leu | Lys | Val | Lys | Ala | Ser | Ala | Ser | Ala | Pro | Pro | Lys | Ile | Asn | |
| | | | 45 | | | | 50 | | | | 55 | | | | | |
| GGT | TCC | TCG | GTC | GGT | CTA | AAG | TCC | GGC | AGT | CTC | AAG | ACT | CAG | GAA | GAT | 304 |
| Gly | Ser | Ser | Val | Gly | Leu | Lys | Ser | Gly | Ser | Leu | Lys | Thr | Gln | Glu | Asp | |
| | 60 | | | | 65 | | | | | 70 | | | | | | |
| ACT | CCT | TCG | GTG | CCT | CCT | CCG | CGG | ACG | TTT | ATC | AAC | CAG | TTG | CCT | GAT | 352 |
| Thr | Pro | Ser | Val | Pro | Pro | Pro | Arg | Thr | Phe | Ile | Asn | Gln | Leu | Pro | Asp | |
| 75 | | | | 80 | | | | | 85 | | | | | 90 | | |
| TGG | AGT | ATG | CTT | CTT | GCT | GCA | ATC | ACT | ACT | GTC | TTC | TTG | GCA | GCA | GAG | 400 |
| Trp | Ser | Met | Leu | Leu | Ala | Ala | Ile | Thr | Thr | Val | Phe | Leu | Ala | Ala | Glu | |
| | | | 95 | | | | | 100 | | | | | 105 | | | |
| AAG | CAG | TGG | ATG | ATG | CTT | GAC | TGG | AAA | CCT | AAG | AGG | CCT | GAC | ATG | CTT | 448 |
| Lys | Gln | Trp | Met | Met | Leu | Asp | Trp | Lys | Pro | Lys | Arg | Pro | Asp | Met | Leu | |
| | | | 110 | | | | 115 | | | | | 120 | | | | |
| GTG | GAC | CCG | TTC | GGA | TTG | GGA | AGT | ATT | GTC | CAG | GGT | GGG | CTT | GTG | TTC | 496 |
| Val | Asp | Pro | Phe | Gly | Leu | Gly | Ser | Ile | Val | Gln | Gly | Gly | Leu | Val | Phe | |
| | | 125 | | | | | 130 | | | | | 135 | | | | |
| AGG | CAA | AAT | TTT | TCT | ATT | AGG | TCC | TAT | GAA | ATA | GGC | GCT | GAT | CGC | ACT | 544 |
| Arg | Gln | Asn | Phe | Ser | Ile | Arg | Ser | Tyr | Glu | Ile | Gly | Ala | Asp | Arg | Thr | |
| | 140 | | | | | 145 | | | | | 150 | | | | | |
| GCA | TCT | ATA | GAG | ACG | GTG | ATG | AAC | CAC | TTG | CAG | GAA | ACG | GCT | CTC | AAT | 592 |
| Ala | Ser | Ile | Glu | Thr | Val | Met | Asn | His | Leu | Gln | Glu | Thr | Ala | Leu | Asn | |
| 155 | | | | | 160 | | | | | 165 | | | | | 170 | |
| CAT | GTT | AAG | AGT | GCT | GGG | CTT | CTT | AAT | GAC | GGC | TTT | GGT | CGT | ACT | CCT | 640 |
| His | Val | Lys | Ser | Ala | Gly | Leu | Leu | Asn | Asp | Gly | Phe | Gly | Arg | Thr | Pro | |
| | | | | 175 | | | | | 180 | | | | | 185 | | |
| GAG | ATG | TTT | AAA | AGG | GAC | CTC | ATT | TGG | GTT | GTC | GCG | AAA | ATG | CAG | GTC | 688 |
| Glu | Met | Phe | Lys | Arg | Asp | Leu | Ile | Trp | Val | Val | Ala | Lys | Met | Gln | Val | |
| | | | 190 | | | | | 195 | | | | | 200 | | | |
| ATG | GTT | AAC | CGC | TAT | CCT | ACT | TGG | GGT | GAC | ACG | GTT | GAA | GTG | AAT | ACT | 736 |
| Met | Val | Asn | Arg | Tyr | Pro | Thr | Trp | Gly | Asp | Thr | Val | Glu | Val | Asn | Thr | |
| | | 205 | | | | | 210 | | | | | 215 | | | | |
| TGG | GTT | GCC | AAG | TCA | GGG | AAA | AAT | GGT | ATG | CGT | CGT | GAT | TGG | CTC | ATA | 784 |
| Trp | Val | Ala | Lys | Ser | Gly | Lys | Asn | Gly | Met | Arg | Arg | Asp | Trp | Leu | Ile | |
| | 220 | | | | | 225 | | | | | 230 | | | | | |
| AGT | GAT | TGC | AAT | ACA | GGA | GAA | ATT | CTA | ACT | AGA | GCT | TCA | AGC | GTG | TGG | 832 |
| Ser | Asp | Cys | Asn | Thr | Gly | Glu | Ile | Leu | Thr | Arg | Ala | Ser | Ser | Val | Trp | |
| 235 | | | | | 240 | | | | | 245 | | | | | 250 | |
| GTC | ATG | ATG | AAT | CAA | AAG | ACA | AGA | AAA | TTG | TCA | AAA | ATT | CCA | GAT | GAG | 880 |
| Val | Met | Met | Asn | Gln | Lys | Thr | Arg | Lys | Leu | Ser | Lys | Ile | Pro | Asp | Glu | |
| | | | | 255 | | | | | 260 | | | | | 265 | | |
| GTT | CGA | CAT | GAG | ATA | GAG | CCT | CAT | TTT | ATA | GAC | TGT | GCT | CCC | GTC | ATT | 928 |
| Val | Arg | His | Glu | Ile | Glu | Pro | His | Phe | Ile | Asp | Cys | Ala | Pro | Val | Ile | |
| | | | 270 | | | | 275 | | | | | 280 | | | | |
| GAA | GAC | GAT | GAC | CGG | AAA | CTC | CGC | AAG | CTG | GAT | GAG | AAG | ACT | GCT | GAC | 976 |
| Glu | Asp | Asp | Asp | Arg | Lys | Leu | Arg | Lys | Leu | Asp | Glu | Lys | Thr | Ala | Asp | |
| | | 285 | | | | | 290 | | | | | 295 | | | | |
| TCC | ATC | CGC | AAG | GGT | CTA | ACT | CCG | AAG | TGG | AAT | GAC | TTG | GAT | GTC | AAT | 1024 |
| Ser | Ile | Arg | Lys | Gly | Leu | Thr | Pro | Lys | Trp | Asn | Asp | Leu | Asp | Val | Asn | |
| | 300 | | | | | 305 | | | | | 310 | | | | | |
| CAG | CAT | GTC | AAC | AAC | GTG | AAG | TAC | ATC | GGG | TGG | ATT | CTC | GAG | AGT | ACT | 1072 |
| Gln | His | Val | Asn | Asn | Val | Lys | Tyr | Ile | Gly | Trp | Ile | Leu | Glu | Ser | Thr | |
| 315 | | | | | 320 | | | | | 325 | | | | | 330 | |
| CCA | CAA | GAA | GTT | CTG | GAG | ACC | CAA | GAG | TTA | TCT | TCC | CTT | ACC | CTG | GAA | 1120 |
| Pro | Gln | Glu | Val | Leu | Glu | Thr | Gln | Glu | Leu | Ser | Ser | Leu | Thr | Leu | Glu | |
| | | | | 335 | | | | | 340 | | | | | 345 | | |
| TAC | AGG | CGG | GAA | TGC | GGA | AGG | GAG | AGT | GTG | CTG | GAG | TCC | CTC | ACT | GCT | 1168 |
| Tyr | Arg | Arg | Glu | Cys | Gly | Arg | Glu | Ser | Val | Leu | Glu | Ser | Leu | Thr | Ala | |
| | | | 350 | | | | | 355 | | | | | 360 | | | |

-continued

```
GTG GAC TCC TCT GGA AAG GGC TTT GGG TCC CAG TTC CAA CAC CTT CTG    1216
Val Asp Ser Ser Gly Lys Gly Phe Gly Ser Gln Phe Gln His Leu Leu
        365                 370                 375

AGG CTT GAG GAT GGA GGT GAG ATC GTG AAG GGG AGA ACT GAG TGG CGA    1264
Arg Leu Glu Asp Gly Gly Glu Ile Val Lys Gly Arg Thr Glu Trp Arg
380                 385                 390

CCC AAG ACT GCA GGT GTC AAT GGG GCA ATA GCA TCC GGG GAG ACC TCA    1312
Pro Lys Thr Ala Gly Val Asn Gly Ala Ile Ala Ser Gly Glu Thr Ser
395                 400                 405                 410

CAT GGA GAC TCT TAGAAGGGAG CCCCGGTCCC TTTCGAGTTC TGCTTTCTTT       1364
His Gly Asp Ser

ATTGTCGGAT GAGCTGAGTG AACGGCAGGT AAGGTAGTAG CAATCAGTGG ATTGTGTAGT  1424

TTATTTGCTG TTTTTCACTT CGGCTCTCTT GTATAAAAAA AAAAAAAAAA AAAAAACTCG  1484

TGCCGAATTC                                                        1494
```

(2) INFORMATION FOR SEQ ID NO: 2:

(i) SEQUENCE CHARACTERISTICS:
        (A) LENGTH: 1404 Base pairs
        (B) TYPE: nucleic acid
        (C) STRANDEDNESS: double stranded
        (D) TOPOLOGY: linear (ii) MOLECULE TYPE:: c-DNA to m-RNA (iii) HYPOTHETICAL: No (iii) ANTI-SENSE: No (vi) ORIGINAL SOURCE:
        (A) ORGANISM: Cuphea lanceolata (vii) IMMEDIATE SOURCE:
        (A) LIBRARY: c-DNA Bank ZAP
        (B) CLONE: ClTE5

(ix) FEATURE:
        (A) NAME/KEY: CDS
        (B) LOCATION: 15..1139

(ix) FEATURE:
        (A) NAME/KEY: Transit-Peptide
        (B) LOCATION: 15..245

(ix) FEATURE:
        (A) NAME/KEY: mature Protein
        (B) LOCATION: 246..1139

(ix) FEATURE:
        (A) NAME/KEY: Stopcodon
        (B) LOCATION: 1140..1142

(xi) SEQUENCE DESCRIPTION: SEQ ID NO: 2:

```
GAATTCGGCA CGAG CTC AAG CCC AAA TCC ATC CCC AAT GGC GGT TTG CAA    50
              Leu Lys Pro Lys Ser Ile Pro Asn Gly Gly Leu Gln
                1                 5                  10

GTT AAG GCA AGC GCC AGT GCC CCT CCT AAG ATC AAT GGT TCC TCG GTC    98
Val Lys Ala Ser Ala Ser Ala Pro Pro Lys Ile Asn Gly Ser Ser Val
         15                 20                  25

GGT CTA AAG TCG GGC GGT CTC AAG ACT CAT GAC GAC GCC CCT TCG GCC   146
Gly Leu Lys Ser Gly Gly Leu Lys Thr His Asp Asp Ala Pro Ser Ala
         30                 35                  40

CCT CCT CCC CGG ACT TTT ATC AAC CAG TTA CCT GAT TGG AGT ATG CTT   194
Pro Pro Pro Arg Thr Phe Ile Asn Gln Leu Pro Asp Trp Ser Met Leu
45                  50                  55                  60

CTT GCT GCA ATC ACT ACT GCC TTC TTG GCA GCA GAG AAG CAG TGG ATG   242
Leu Ala Ala Ile Thr Thr Ala Phe Leu Ala Ala Glu Lys Gln Trp Met
                65                  70                  75
```

```
ATG CTT GAT TGG AAA CCG AAG AGG CTT GAC ATG CTT GAG GAC CCG TTC         290
Met Leu Asp Trp Lys Pro Lys Arg Leu Asp Met Leu Glu Asp Pro Phe
            80                  85                  90

GGA TTG GGA AGG ATT GTT CAG GAT GGG CTT GTG TTC AGG CAG AAT TTT         338
Gly Leu Gly Arg Ile Val Gln Asp Gly Leu Val Phe Arg Gln Asn Phe
        95                 100                 105

TCG ATT AGG TCC TAC GAA ATA GGC GCC GAT CGC ACT GCG TCT ATT GAG         386
Ser Ile Arg Ser Tyr Glu Ile Gly Ala Asp Arg Thr Ala Ser Ile Glu
    110                 115                 120

ACG GTG ATG AAT CAC TTG CAG GAA ACA GCT CTC AAT CAT GTT AAG ACT         434
Thr Val Met Asn His Leu Gln Glu Thr Ala Leu Asn His Val Lys Thr
125                 130                 135                 140

GCT GGG CTT TCT AAT GAC GGC TTT GGT CGT ACT CCT GAG ATG TAT AAA         482
Ala Gly Leu Ser Asn Asp Gly Phe Gly Arg Thr Pro Glu Met Tyr Lys
                145                 150                 155

AGG GAC CTT ATT TGG GTT GTT GCG AAA ATG CAG GTC ATG GTT AAC CGC         530
Arg Asp Leu Ile Trp Val Val Ala Lys Met Gln Val Met Val Asn Arg
                160                 165                 170

TAT CCT ACT TGG GGT GAC ACA GTT GAA GTG AAT ACT TGG GTT GCC AAG         578
Tyr Pro Thr Trp Gly Asp Thr Val Glu Val Asn Thr Trp Val Ala Lys
            175                 180                 185

TCA GGG AAA AAT GGT ATG CGT CGT GAC TGG CTC ATA AGT GAT TGC AAT         626
Ser Gly Lys Asn Gly Met Arg Arg Asp Trp Leu Ile Ser Asp Cys Asn
        190                 195                 200

ACA GGA GAG ATT CTT ACA AGA GCA TCA AGC GTG TGG GTA ATG ATG AAT         674
Thr Gly Glu Ile Leu Thr Arg Ala Ser Ser Val Trp Val Met Met Asn
205                 210                 215                 220

CAA AAG ACA AGA AAA TTG TCA AAA ATT CCA GAT GAG GTT CGA CGT GAG         722
Gln Lys Thr Arg Lys Leu Ser Lys Ile Pro Asp Glu Val Arg Arg Glu
                225                 230                 235

ATA GAG CCT CAT TTT GTG GAC TCT GCT CCC GTC ATT GAA GAC GAT GAC         770
Ile Glu Pro His Phe Val Asp Ser Ala Pro Val Ile Glu Asp Asp Asp
                240                 245                 250

CGG AAA CTT CCC AAG CTG GAT GAG AAG AGT GCT GAC TCC ATC CGC AAG         818
Arg Lys Leu Pro Lys Leu Asp Glu Lys Ser Ala Asp Ser Ile Arg Lys
            255                 260                 265

GGT CTA ACT CCG AGG TGG AAT GAT TTG GAT GTC AAT CAG CAC GTC AAC         866
Gly Leu Thr Pro Arg Trp Asn Asp Leu Asp Val Asn Gln His Val Asn
        270                 275                 280

AAC GTG AAG TAC ATC GGG TGG ATT CTT GAG AGT ACT CCA CCA GAA GTT         914
Asn Val Lys Tyr Ile Gly Trp Ile Leu Glu Ser Thr Pro Pro Glu Val
285                 290                 295                 300

CTG GAG ACC CAG GAG TTA TGT TCC CTT ACC CTG GAA TAC AGG CGG GAA         962
Leu Glu Thr Gln Glu Leu Cys Ser Leu Thr Leu Glu Tyr Arg Arg Glu
                305                 310                 315

TGT GGA AGG GAG AGC GTG CTG GAG TCC CTC ACT GCT GTG GAC CCC TCT        1010
Cys Gly Arg Glu Ser Val Leu Glu Ser Leu Thr Ala Val Asp Pro Ser
            320                 325                 330

GGA GAG GGC TAT GGA TCC CAG TTT CAG CAC CTT CTG CGG CTT GAG GAT        1058
Gly Glu Gly Tyr Gly Ser Gln Phe Gln His Leu Leu Arg Leu Glu Asp
        335                 340                 345

GGA GGT GAG ATC GTG AAG GGG AGA ACT GAG TGG CGA CCA AAG AAT GCT        1106
Gly Gly Glu Ile Val Lys Gly Arg Thr Glu Trp Arg Pro Lys Asn Ala
350                 355                 360

GGA ATC AAT GGG GGG GTA CCG TCC GAG GAG TCC TAACCTGGAG ACTACTCTTA      1159
Gly Ile Asn Gly Gly Val Pro Ser Glu Glu Ser
365                 370                 375

GAAGGAGGAG CCCTGGGCTG GCCCCTTTGG AGTTATGCTT TCTTTTATTG TGGGATGAGC      1219

TGAGTGAAGG GCAGGTAAGA TTAAGATAGT AGCAATCGGG AGATTGTGTA GTTTGTTTGC      1279
```

```
TGCTTTTCAC TTTGGCTCTC TTGTATAATA TCATGGTCGT CGTCTTTGTA TCCTCGCATG    1339

GTCCGGTTTG ATTTATACAT TATATTCTTT CTATTTGTTT CAAAAAAAAA AAAAAAAAAC    1399

TCGAG                                                                 1404
```

(2) INFORMATION FOR SEQ ID NO: 3:

(i) SEQUENCE CHARACTERISTICS:
        (A) LENGTH: 1066 Base pairs
        (B) TYPE: nucleic acid
        (C) STRANDEDNESS: double stranded
        (D) TOPOLOGY: linear (ii) MOLECULE TYPE:: c-DNA to m-RNA (iii) HYPOTHETICAL: No (iii) ANTI-SENSE: No (vi) ORIGINAL SOURCE:
        (A) ORGANISM: Cuphea lanceolata (vii) IMMEDIATE SOURCE:
        (A) LIBRARY: c-DNA Bank ZAP
        (B) CLONE: ClTE12

(ix) FEATURE:
        (A) NAME/KEY: CDS
        (B) LOCATION: 15..875

(ix) FEATURE:
        (A) NAME/KEY: Stopcodon
        (B) LOCATION: 876..878

(xi) SEQUENCE DESCRIPTION: SEQ ID NO: 3:

```
GAATTCGGCA CGAG GTT CGG GAT GGG CTC GTG TCC AGA CAG AGT TTT TTG       50
               Val Arg Asp Gly Leu Val Ser Arg Gln Ser Phe Leu
                1               5                  10

ATT AGA TCT TAT GAA ATA GGC GCT GAT CGA ACA GCC TCT ATA GAG ACG       98
Ile Arg Ser Tyr Glu Ile Gly Ala Asp Arg Thr Ala Ser Ile Glu Thr
            15                  20                  25

CTG ATG AAC CAC TTG CAG GAA ACA TCT ATC AAT CAT TGT AAG AGT TTG      146
Leu Met Asn His Leu Gln Glu Thr Ser Ile Asn His Cys Lys Ser Leu
 30                  35                  40

GGT CTT CTC AAT GAC GGC TTT GGT CGT ACT CCT GGG ATG TGT AAA AAC      194
Gly Leu Leu Asn Asp Gly Phe Gly Arg Thr Pro Gly Met Cys Lys Asn
 45                  50                  55                  60

GAC CTC ATT TGG GTG CTT ACA AAA ATG CAG ATC ATG GTG AAT CGC TAC      242
Asp Leu Ile Trp Val Leu Thr Lys Met Gln Ile Met Val Asn Arg Tyr
                65                  70                  75

CCA ACT TGG GGC GAT ACT GTT GAG ATC AAT ACC TGG TTC TCT CAG TCG      290
Pro Thr Trp Gly Asp Thr Val Glu Ile Asn Thr Trp Phe Ser Gln Ser
            80                  85                  90

GGG AAA ATC GGT ATG GCT AGC GAT TGG CTA ATA AGT GAT TGC AAC ACA      338
Gly Lys Ile Gly Met Ala Ser Asp Trp Leu Ile Ser Asp Cys Asn Thr
         95                 100                 105

GGA GAA ATT CTT ATA AGA GCA ACG AGC GTG TGG GCT ATG ATG AAT CAA      386
Gly Glu Ile Leu Ile Arg Ala Thr Ser Val Trp Ala Met Met Asn Gln
    110                 115                 120

AAG ACG AGA AGA TTC TCA AGA CTT CCA TAC GAG GTT CGC CAG GAG TTA      434
Lys Thr Arg Arg Phe Ser Arg Leu Pro Tyr Glu Val Arg Gln Glu Leu
125                 130                 135                 140

ACA CCT CAT TTT GTG GAC TCT CCT CAT GTC ATT GAA GAC AAT GAT CAG      482
Thr Pro His Phe Val Asp Ser Pro His Val Ile Glu Asp Asn Asp Gln
                145                 150                 155

AAA TTG CAT AAG TTT GAT GTG AAG ACT GGT GAT TCC ATT CGC AAG GGT      530
```

```
Lys Leu His Lys Phe Asp Val Lys Thr Gly Asp Ser Ile Arg Lys Gly
            160                 165                 170

CTA ACT CCG AGG TGG AAT GAC TTG GAT GTG AAT CAG CAC GTA AGC AAC       578
Leu Thr Pro Arg Trp Asn Asp Leu Asp Val Asn Gln His Val Ser Asn
            175                 180                 185

GTG AAG TAC ATT GGG TGG ATT CTC GAG AGT ATG CCA ATA GAA GTT TTG       626
Val Lys Tyr Ile Gly Trp Ile Leu Glu Ser Met Pro Ile Glu Val Leu
            190                 195                 200

GAG ACC CAG GAG CTA TGC TCT CTC ACC GTT GAA TAT AGG CGG GAA TGC       674
Glu Thr Gln Glu Leu Cys Ser Leu Thr Val Glu Tyr Arg Arg Glu Cys
205                 210                 215                 220

GGA ATG GAC AGT GTG CTG GAG TCC GTG ACT GCT GTG GAT CCC TCA GAA       722
Gly Met Asp Ser Val Leu Glu Ser Val Thr Ala Val Asp Pro Ser Glu
                225                 230                 235

AAT GGA GGC CGG TCT CAG TAC AAG CAC CTT TTG CGG CTT GAG GAT GGG       770
Asn Gly Gly Arg Ser Gln Tyr Lys His Leu Leu Arg Leu Glu Asp Gly
            240                 245                 250

ACT GAT ATC GTG AAG AGC AGA ACT GAG TGG CGA CCG AAG AAT GCA GGA       818
Thr Asp Ile Val Lys Ser Arg Thr Glu Trp Arg Pro Lys Asn Ala Gly
            255                 260                 265

ACT AAC GGG GCG ATA TCA ACA TCA ACA GCA AAG ACT TCA AAT GGA AAC       866
Thr Asn Gly Ala Ile Ser Thr Ser Thr Ala Lys Thr Ser Asn Gly Asn
            270                 275                 280

TCG GCC TCT TAGAAGAGTC TCGGGACCCT TCCAAGATGT GCATTTCTTT              915
Ser Ala Ser
285

TCTCTTTCTC ATTGTCTGCT GAGCTGAAAG AAGAGCATGT GGTTGCAATC AGTAAATTGT     975

GTAGTTCGCT TTGCTTCGCT CCTTTGTATA ATAACATGGT CAGTCGTCTT TGTATCAAAA    1035

AAAAAAAAAA AAAAAAAAA AAAAACTCGA G                                   1066

(2) INFORMATION FOR SEQ ID NO: 4:

(i) SEQUENCE CHARACTERISTICS:
        (A) LENGTH: 4098 Base pairs
        (B) TYPE: nucleic acid
        (C) STRANDEDNESS: double stranded
        (D) TOPOLOGY: linear (ii) MOLECULE TYPE:: DNS (genomic)

(iii) HYPOTHETICAL: No (iii) ANTI-SENSE: No (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClTEg1

(ix) FEATURE:
        (A) NAME/KEY: CDS
        (B) LOCATION: join(1797..2294, 2658..2791, 2898..3011, 3132
            ..3303, 3391..3459, 3672..3941)

(ix) FEATURE:
        (A) NAME/KEY: Startcodon
        (B) LOCATION: 1797..1799

(ix) FEATURE:
        (A) NAME/KEY: exon II
        (B) LOCATION: 1787..2294

(ix) FEATURE:
        (A) NAME/KEY: intron II
        (B) LOCATION: 2295..2657
```

```
         (ix) FEATURE:
               (A) NAME/KEY: exon III
               (B) LOCATION: 2658..2791

(ix) FEATURE:
               (A) NAME/KEY: intron III
               (B) LOCATION: 2792..2897

(ix) FEATURE:
               (A) NAME/KEY: exon IV
               (B) LOCATION: 2898..3011

(ix) FEATURE:
               (A) NAME/KEY: intron IV
               (B) LOCATION: 3012..3131

(ix) FEATURE:
               (A) NAME/KEY: exon V
               (B) LOCATION: 3132..3303

(ix) FEATURE:
               (A) NAME/KEY: intron V
               (B) LOCATION: 3304..3390

(ix) FEATURE:
               (A) NAME/KEY: exon VI
               (B) LOCATION: 3391..3459

(ix) FEATURE:
               (A) NAME/KEY: intron VI
               (B) LOCATION: 3460..3671

(ix) FEATURE:
               (A) NAME/KEY: exon VII
               (B) LOCATION: 3672..3941

(ix) FEATURE:
               (A) NAME/KEY: Stopcodon
               (B) LOCATION: 3942..3944

(xi) SEQUENCE DESCRIPTION: SEQ ID NO: 4:

CACCCATAAG AACCCAAAAG TCTGAAATAC AGTCAAAACC CGTAAAATTT TGATATATTA      60

TCGAATATTT TGGGATATTT GGTCCTTATG AGTGTTCGAG GGATATTTCA AATTTTACGA     120

ATATTCGGGA ATATTTCGCT ATTTAAAATT TTGCGGGATA TATTTGTAAT ATTTTATGAA     180

TTATTGAAAT ATTTTTTGAA ATTTTAAAAT ATTTTTTAAA ATTTAAATAT ATTTTAAATT     240

CTTTTAAAAA AAATATTTTT AAATATTATA AAATTAGTTT TTAAAATTTT TTAAATATTT     300

TAAAATTAGT TTTTTTTATT TTTAAAATAT TGTTGAATTT TTAAAATATT TTTTGGTTTT     360

AAAAATATAT TTAAAAGTTT TTAAATATTT TTTGAATTTT TGAAATATTG AAAAAATTTT     420

GTTGGAGATA ACCGGAGAAT TTATATATAT ATATATATAT ATATATATAT ATATATATTT     480

CGTCCATTTC GGTTAAACCA AACGTAGTTC GTAACAGAAT GATAAACGTG ATCTATGGAA     540

TGAAAGTTTA AGAGCAAACG AAGCTATTAT TTTAATTTAA AGACAAAAGT AGTGACAATT     600

TATACTTTTA AGGCAAGTTT GACCGTTAAG TCTATTTTTT ATATTGACGG GACGTGGCCA     660

TGTAATTGGT TACTTTGTCG ATGTATGCCA TGTAAGAATC ATACGCCAAC GTTCGTTAAC     720

GCCATTAACC ATACGTCATG TAAGAATATA CGTTCATTAG AAGGAACATG AAAGAAAGGG     780

TACATATTCG ATCTATATAC CGATCTATAT ACCATAGTAT TCCATATAAA TACCTTATTT     840

AGAAATACCA TATTATATAG ATATCAACGT CATTAATAAA AAATAGAAGG TTGGACCCTG     900

CATGTTACGA AATATAATGA GTTATATTTT AAATTTTGCT TTTGGATAAG TGATCCCGAA     960

AATAAGTGGA CGAAGTAATT AACCCAAATT TTTAAGCTCA AACTGATACA GTTGGATTCA    1020

TAGTTGAGGA AATGAAAACA GCTGAAGATC GCAAAGTTTC CATTGCCATA CTCATACCTC    1080

TTCATTCAGC TATGTCCCTT CCCTTGGCTT CCTATTTAAG CTGTTGTTTG TGTATGTCGC    1140
```

```
CATTTGGCCC CTCCCTCCCC TCCTCTTCAG GTATACCCAC GGCCCTCATC ATTCTCTCAC    1200

TACGTGTCTG TGTTTCCATC CCATTCCCCG CCCCGTCTCC TTTCCTTCCT TCACGGGACT    1260

TTGCTTTTGC ATACCCAGTG AACTGAACCC ACCCACCCCC AGTCACCCAG TTGTCATCTT    1320

TTTTCTGCAA AGCCTCTCTG CTTTCTTCGT TTACCGTCGT CCTGAGCCCA TAGAAAAGTT    1380

TGCCCATTTC CTCCTCGTGT TGATCGACCT CATGTCCCGT TTCTTGCCAA ATGTGCGGCC    1440

CTTCTTCTCC TGCCCACTTT CTGTTTTTTA ATGTTATGCT CCGAGCCACG TTTCTTTGAT    1500

TCTCTGTTCT CCTCACGGCG CCTTCCGGGC CACCGTCACT GTCCCCCTTC TTTATATGGC    1560

TTCCGTTTTC CTTCGTTGCT GGATATCCCA TCCCATGTTC ATCTGAGTTT GCTGTCTACC    1620

ATTTTCCCTG TATGTTATTT CCATGCATGC ATGCATGTCT ATGGCTTCCT TGTAGAAATG    1680

TGTTGTGTTT TGTTATAAAG CTTCCATCTT TCCCTTCTGT TTGAATCCGA GGTTGTCGTT    1740

TTAATGCAAT TAAAGCTTCT GCTAACTGAC CCTCTTGTGT TTACAGGCGA AGAAAC        1796

ATG GTG GCT GCT GCA GCA ACT TCT GCA TTC TTC CCT GTT CCA GCC CCG     1844
Met Val Ala Ala Ala Ala Thr Ser Ala Phe Phe Pro Val Pro Ala Pro
 1               5                  10                  15

GGA ACC TCC CCT AAA CCC GGG AAG TCC GGC AAC TGG CCA TCG AGC TTG     1892
Gly Thr Ser Pro Lys Pro Gly Lys Ser Gly Asn Trp Pro Ser Ser Leu
             20                  25                  30

AGC CCT ACC TTC AAG CCC AAG TCA ATC CCC AAT GCT GGA TTT CAG GTT     1940
Ser Pro Thr Phe Lys Pro Lys Ser Ile Pro Asn Ala Gly Phe Gln Val
         35                  40                  45

AAG GCA AAT GCC AGT GCC CAT CCT AAG GCT AAC GGT TCT GCA GTA AAT     1988
Lys Ala Asn Ala Ser Ala His Pro Lys Ala Asn Gly Ser Ala Val Asn
     50                  55                  60

CTA AAG TCT GGC AGC CTC AAC ACT CAG GAG GAC ACT TCG TCG TCC CCT     2036
Leu Lys Ser Gly Ser Leu Asn Thr Gln Glu Asp Thr Ser Ser Ser Pro
 65                  70                  75                  80

CCT CCC CGG GCT TTC CTT AAC CAG TTG CCT GAT TGG AGT ATG CTT CTG     2084
Pro Pro Arg Ala Phe Leu Asn Gln Leu Pro Asp Trp Ser Met Leu Leu
                 85                  90                  95

ACT GCA ATC ACG ACC GTC TTC GTG GCG GCA GAG AAG CAG TGG ACT ATG     2132
Thr Ala Ile Thr Thr Val Phe Val Ala Ala Glu Lys Gln Trp Thr Met
             100                 105                 110

CTT GAT AGG AAA TCT AAG AGG CCT GAC ATG CTC GTG GAC TCG GTT GGG     2180
Leu Asp Arg Lys Ser Lys Arg Pro Asp Met Leu Val Asp Ser Val Gly
         115                 120                 125

TTG AAG AGT ATT GTT CGG GAT GGG CTC GTG TCC AGA CAG AGT TTT TTG     2228
Leu Lys Ser Ile Val Arg Asp Gly Leu Val Ser Arg Gln Ser Phe Leu
     130                 135                 140

ATT AGA TCT TAT GAA ATA GGC GCT GAT CGA ACA GCC TCT ATA GAG ACG     2276
Ile Arg Ser Tyr Glu Ile Gly Ala Asp Arg Thr Ala Ser Ile Glu Thr
145                 150                 155                 160

CTG ATG AAC CAC TTG CAG GTACTGCTTT GAAACTATTC ATTCATCGCA             2324
Leu Met Asn His Leu Gln
                165

TATGCTAGTG ATCAGTAAAT GAGCCATGAC TAGATGATGA AATAGATAAC ACCGATTGCC    2384

GGTACAACGA GCTAATTGTT CCATTTTAAT TTAGAAGTGC TCTTTTCTTG TTCATGACGA    2444

GGTTGGTATC CCAGGGTGAG ATTTGTCAGG TTGATTCAAT GAAAGGGCTA ATTTTCGACG    2504

CGTACTATGA TAGTTTTAAT GCTCTCATTC GAACTTGAAA TGACTAAGCA TTCTGATGAG    2564

AAGTATTTAA TCTAAAATGC TTGCATTAGT TTTGCTTATA TTTTCTCGTT AACTCGGTTG    2624

TCTTTATTCT TGTTTTTTTT TTTCTCTTAA CAG GAA ACA TCT ATC AAT CAT TGT   2678
                                    Glu Thr Ser Ile Asn His Cys
                                                        170
```

-continued

| | |
|---|---|
| AAG AGT TTG GGT CTT CTC AAT GAC GGC TTT GGT CGT ACT CCT GGG ATG<br>Lys Ser Leu Gly Leu Leu Asn Asp Gly Phe Gly Arg Thr Pro Gly Met<br>175                    180                  185 | 2726 |
| TGT AAA AAC GAC CTC ATT TGG GTG CTT ACA AAA ATG CAG ATC ATG GTG<br>Cys Lys Asn Asp Leu Ile Trp Val Leu Thr Lys Met Gln Ile Met Val<br>190                  195                200                205 | 2774 |
| AAT CGC TAC CCA ACT  TG GTAAGTTTGT CACTGGCTGG TTTGTCTTTT<br>Asn Arg Tyr Pro Thr  Trp<br>210 | 2821 |
| GGTCCGTAAG TGCCTCTTAC AATACTAGTT GTAAACATAG TGGAATGTAA TGGCCTGTAT | 2881 |
| GTGATCTTTA TGGTAG G GGC GAT ACT GTT GAG ATC AAT ACC TGG TTC TCT<br>                    Gly Asp Thr Val Glu Ile Asn Thr Trp Phe Ser<br>                              215                  220 | 2931 |
| CAG TCG GGG AAA ATC GGT ATG GCT AGC GAT TGG CTA ATA AGT GAT TGC<br>Gln Ser Gly Lys Ile Gly Met Ala Ser Asp Trp Leu Ile Ser Asp Cys<br>        225                230                235 | 2979 |
| AAC ACA GGA GAA ATT CTT ATA AGA GCA ACG  AG GTATTATTAA<br>Asn Thr Gly Glu Ile Leu Ile Arg Ala Thr  Ser<br>240                  245 | 3021 |
| TTCTGGCTCT GAGTTTACAT TCTCAAAACC TTCTGATGCT CGATCAGTGA GCAGACATTT | 3081 |
| GGCATGTTTT ATGTGTAAAG TGGAGTCATG TCACTCTCAT ATTATCGCAG C GTG TGG<br>                                                              Val Trp<br>                                                                 250 | 3138 |
| GCT ATG ATG AAT CAA AAG ACG AGA AGA TTC TCA AGA CTT CCA TAC GAG<br>Ala Met Met Asn Gln Lys Thr Arg Arg Phe Ser Arg Leu Pro Tyr Glu<br>                255                  260                  265 | 3186 |
| GTT CGC CAG GAG TTA ACA CCT CAT TTT GTG GAC TCT CCT CAT GTC ATT<br>Val Arg Gln Glu Leu Thr Pro His Phe Val Asp Ser Pro His Val Ile<br>                270                  275                  280 | 3234 |
| GAA GAC AAT GAT CAG AAA TTG CAT AAG TTT GAT GTG AAG ACT GGT GAT<br>Glu Asp Asn Asp Gln Lys Leu His Lys Phe Asp Val Lys Thr Gly Asp<br>285                    290                  295 | 3282 |
| TCC ATT CGC AAG GGT CTA ACT GTAAGTCCCT ATCTTTCACT GTGATATTAG<br>Ser Ile Arg Lys Gly Leu Thr<br>300                    305 | 3333 |
| GGCGGTTTTT ATGAAATATC GTGTCTCTGA GACGTTCTTC CACTTCATGG TTTGTAG | 3390 |
| CCG AGG TGG AAT GAC TTG GAT GTG AAT CAG CAC GTA AGC AAC GTG AAG<br>Pro Arg Trp Asn Asp Leu Asp Val Asn Gln His Val Ser Asn Val Lys<br>                310                  315                  320 | 3438 |
| TAC ATT GGG TGG ATT CTC GAG GTACCCTTTT CATCGCACGC ACGAGAACAA<br>Tyr Ile Gly Trp Ile Leu Glu<br>                325 | 3489 |
| CTGATATATT TTTTGGTTAA TGATGATAAG ATCAATAAAC TTAGATATTG AATGCAAGTA | 3549 |
| TCTGCTAGCT AGCACATGAG ATATTACTTA AATATCGTAG ACTAGTATCG CCCCGAGTTT | 3609 |
| GTCAAAGCTT ACTTTAGGAT TCCGCTTTAC AGATCTTTGA TCTAGCCGAA TTCTTGTTGC | 3669 |
| AG AGT ATG CCA ATA GAA GTT TTG GAG ACC CAG GAG CTA TGC TCT CTC<br>   Ser Met Pro Ile Glu Val Leu Glu Thr Gln Glu Leu Cys Ser Leu<br>       330                  335                  340 | 3716 |
| ACC GTT GAA TAT AGG CGG GAA TGC GGA ATG GAC AGT GTG CTG GAG TCC<br>Thr Val Glu Tyr Arg Arg Glu Cys Gly Met Asp Ser Val Leu Glu Ser<br>345                    350                  355                360 | 3764 |
| GTG ACT GCT GTG GAT CCC TCA GAA AAT GGA GGC CGG TCT CAG TAC AAG<br>Val Thr Ala Val Asp Pro Ser Glu Asn Gly Gly Arg Ser Gln Tyr Lys<br>                365                  370                  375 | 3812 |
| CAC CTT TTG CGG CTT GAG GAT GGG ACT GAT ATC GTG AAG AGC AGA ACT<br>His Leu Leu Arg Leu Glu Asp Gly Thr Asp Ile Val Lys Ser Arg Thr<br>                380                  385                  390 | 3860 |

```
                                           -continued

GAG TGG CGA CCG AAG AAT GCA GGA ACT AAC GGG GCG ATA TCA ACA TCA        3908
Glu Trp Arg Pro Lys Asn Ala Gly Thr Asn Gly Ala Ile Ser Thr Ser
        395                 400                 405

ACA GCA AAG ACT TCA AAT GGA AAC TCG GCC TCT TAGAAGAGTC TCGGGACCCT      3961
Thr Ala Lys Thr Ser Asn Gly Asn Ser Ala Ser
    410                 415

TCCAAGATGT GCATTTCTTT TCTCTTTCTC ATTGTCTGCT GAGCTGAAAG AAGAGCATGT      4021

GGTTGCAATC AGTAAATTGT GTAGTTCGCT TTGCTTCGCT CCTTTGTATA ATAACATGGT      4081

CAGTCGTCTT TGTATCA                                                    4098

(2) INFORMATION FOR SEQ ID NO: 5:

(i) SEQUENCE CHARACTERISTICS:
         (A) LENGTH: 928 Base pairs
         (B) TYPE: nucleic acid
         (C) STRANDEDNESS: double stranded
         (D) TOPOLOGY: linear (ii) MOLECULE TYPE:: DNA (genomic)

(iii) HYPOTHETICAL: No (iii) ANTI-SENSE: No (vi) ORIGINAL SOURCE:
         (A) ORGANISM: Cuphea lanceolata (vii) IMMEDIATE SOURCE:
         (A) LIBRARY: genomic Lambda FIX II
         (B) CLONE: ClTEg4

(ix) FEATURE:
         (A) NAME/KEY: CDS
         (B) LOCATION: 8..502

(ix) FEATURE:
         (A) NAME/KEY: Startcodon
         (B) LOCATION: 8..10

(ix) FEATURE:
         (A) NAME/KEY: exon II
         (B) LOCATION: 1..502

(ix) FEATURE:
         (A) NAME/KEY: intron II
         (B) LOCATION: 503..928

(xi) SEQUENCE DESCRIPTION: SEQ ID NO: 5:

AAAAATC ATG GTG GCT ACC GCT GCA AGT TCT GCA TTC TTC CCC GTG CCA          49
        Met Val Ala Thr Ala Ala Ser Ser Ala Phe Phe Pro Val Pro
         1               5                  10

TCT GCC GAC ACC TCC TCC AGA CCC GGA AAG CTC GGT AAT GGT CCA TCG          97
Ser Ala Asp Thr Ser Ser Arg Pro Gly Lys Leu Gly Asn Gly Pro Ser
 15              20                  25                  30

AGC TTC AGC CCC CTC AAG CCC AAA TCC ATC CCC AAT GGC GGT TTG CAG         145
Ser Phe Ser Pro Leu Lys Pro Lys Ser Ile Pro Asn Gly Gly Leu Gln
             35                  40                  45

GTT AAG GCA AGC GCC AGT GCC CCT CCT AAG ATC AAT GGT TCC TCG GTC         193
Val Lys Ala Ser Ala Ser Ala Pro Pro Lys Ile Asn Gly Ser Ser Val
         50                  55                  60

GGT CTA AAG TCG GGC GGT CTC AAG ACT CAT GAC GAC GCC CCT TCG GCC         241
Gly Leu Lys Ser Gly Gly Leu Lys Thr His Asp Asp Ala Pro Ser Ala
     65                  70                  75

CCT CCT CCC CGG ACT TTT ATC AAC CAG TTG CCT GAT TGG AGT ATG CTT         289
Pro Pro Pro Arg Thr Phe Ile Asn Gln Leu Pro Asp Trp Ser Met Leu
 80                  85                  90

CTT GCT GCA ATC ACT ACT GCC TTC TTG GCA GCA GAG AAG CAG TGG ATG         337
Leu Ala Ala Ile Thr Thr Ala Phe Leu Ala Ala Glu Lys Gln Trp Met
```

```
                    95              100             105                110
ATG CTT GAT TGG AAA CCG AAG AGG CTT GAC ATG CTT GAG GAC CCG TTC        385
Met Leu Asp Trp Lys Pro Lys Arg Leu Asp Met Leu Glu Asp Pro Phe
                115                 120                 125

GGA TTG GGA AGG ATT GTT CAG GAT GGG CTT GTG TTC AGG CAG AAT TTT        433
Gly Leu Gly Arg Ile Val Gln Asp Gly Leu Val Phe Arg Gln Asn Phe
                130                 135                 140

TCG ATT AGG TCC TAC GAA ATA GGC GCC GAT CGC ACT GCG TCT ATT GAG        481
Ser Ile Arg Ser Tyr Glu Ile Gly Ala Asp Arg Thr Ala Ser Ile Glu
                145                 150                 155

ACG GTG ATG AAT CAC TTG CAG GTAATGGTGC ATGCTGCTTT TAAACTACTC           532
Thr Val Met Asn His Leu Gln
            160             165

AATTCATGAA ATGCTTATGG CCAGTAACTG AGCCATACTT GACTATGGCC TACCCAATTT      592

AATGGTGAAT TTGAGAAAGA GAAGGGTTGT ATTGCATGCA TTCCTTTCTC TGTTGTCATA      652

GAGGTGATTC AGTATAGGTT TAACTCGTGT CAGTTTCATC GTATATGCAC TCTTTTCATG      712

ATCACTTTGG TTTCTTATGG CGAGATTTGA GAATCATCTG CTCTACTTTT TTTTTATTAA      772

ATTTAAGCAT TATGAAATTT TATGTGGAAC TTTTTACTTA TGTGACAGTA AACCCAGGAA      832

GGAACTCTCG TTTCATTTGA AAACTGGATT AGTTTTCTGA TATTTATGAA TTTCTAAAAA      892

ATTTGCATTA GTTTGTTTAT AAGTTTGGTT GAATTC                                928

(2) INFORMATION FOR SEQ ID NO: 6:

(i) SEQUENCE CHARACTERISTICS:
        (A) LENGTH: 4643 Base pairs
        (B) TYPE: nucleic acid
        (C) STRANDEDNESS: double stranded
        (D) TOPOLOGY: linear (ii) MOLECULE TYPE: DNA (genomic)

(iii) HYPOTHETICAL: No (iii) ANTI-SENSE: No (vi) ORIGINAL SOURCE:
        (A) ORGANISM: Cuphea lanceolata (vii) IMMEDIATE SOURCE:
        (A) LIBRARY:genomic Lambda FIX II
        (B) CLONE: ClTEg7

(ix) FEATURE:
        (A) NAME/KEY: CDS
        (B) LOCATION: join(783..1277, 1787..1920, 2120..2233, 2352
            ..2523, 2615..2683, 2861..3118)

(ix) FEATURE:
        (A) NAME/KEY: Startcodon
        (B) LOCATION: 783..785

(ix) FEATURE:
        (A) NAME/KEY: exon II
        (B) LOCATION: 773..1277

(ix) FEATURE:
        (A) NAME/KEY: intron II
        (B) LOCATION: 1278..1786

(ix) FEATURE:
        (A) NAME/KEY: exon III
        (B) LOCATION: 1787..1920

(ix) FEATURE:
        (A) NAME/KEY: intron III
        (B) LOCATION: 1921..2119
```

(ix) FEATURE:
 (A) NAME/KEY: exon IV
 (B) LOCATION: 2120..2233

(ix) FEATURE:
 (A) NAME/KEY: intron IV
 (B) LOCATION: 2234..2351

(ix) FEATURE:
 (A) NAME/KEY: exon V
 (B) LOCATION: 2352..2523

(ix) FEATURE:
 (A) NAME/KEY: intron V
 (B) LOCATION: 2524..2614

(ix) FEATURE:
 (A) NAME/KEY: exon VI
 (B) LOCATION: 2615..2683

(ix) FEATURE:
 (A) NAME/KEY: intron VI
 (B) LOCATION: 2684..2860

(ix) FEATURE:
 (A) NAME/KEY: exon VII
 (B) LOCATION: 2861..3118

(ix) FEATURE:
 (A) NAME/KEY: Stopcodon
 (B) LOCATION: 3119..3121

(xi) SEQUENCE DESCRIPTION: SEQ ID NO: 6:

```
GTCGACTCGA TCCTTTCCTC CCGCTCGTAA TGACCCTTTA GCCCCCTTTG CCTTCTTCAA      60

ATCCTCCTTT CCTTTCCCTT CTTCCTCTCT GGGAAGCTTA AAGCTTTGTC CCCCACAACC     120

TCTTTCCCGC ATTCGTTGAG CTGTTTTTTT GTCGCCATTC GCCTCTCCTC TCCTCTCCTC     180

TCCTCTTCAG GTTCGCCCCT ATCTCTCTCC CTCTCTCTTG TTTCGTCTCT TTGCCGGATT     240

TGCAAACCCA TTGAATCCAG CTTGAGCCAC CCAATTGGTT ATAGATCTGC AAAGTCCCTT     300

TTTTCCCCCT TCTCCGGCGC CGGAGCCCGT TTAGAAGTTC CCCATTTTCC ATTTTTTTTT     360

CTCTTTTTTG CTGTCGGGTT GATGTCTCCT TGTTAGATCT GCCGAATGTC AGGCCTTTCC     420

TGTCGTTTTT CAATCTTCTC TGATGATTTT TGACCCAGGT TCCTTTGTTT ATGTGTTCTT     480

CTTCTTTGGA TGTTTCCTTC TTATCCCATC ATCAAAGTTT CTCTTTTTTT CCCAATGATT     540

GTTGGGTCTT CCATCTTATT TGATTATGTT GTTTCGATGA TATCCCATGT TTATCTGCGT     600

TTTTCGAGCG ATTTTTCGGT CGCCATTTCC CTGCATGTCG GTGGCATTGG ATATTCTTGT     660

AACAATCTGA ATGGCATGTG TTGTGGTGAA AGCTTGGATC TTTGCCCTCT GTTTAAATCC     720

TGCGTTTTCG GTTTAATCTA ATTGAAGATT GATCATTTTT CTGTGATTGC AGTTGGAAAA     780

CA ATG GTG GCC ACC GCT GCA AGT TCT GCA TTC TTC CCC CTG CCG TCC      827
   Met Val Ala Thr Ala Ala Ser Ser Ala Phe Phe Pro Leu Pro Ser
   1               5                  10                  15

CCG GAC ACC TCC TCT AGG CCG GGA AAG CTC GGA AAT GGG TCA TCG AGC      875
Pro Asp Thr Ser Ser Arg Pro Gly Lys Leu Gly Asn Gly Ser Ser Ser
               20                  25                  30

TTG AGC CCC CTC AAG CCC AAA TTT GTC GCC AAT GCC GGG TTG AAG GTT      923
Leu Ser Pro Leu Lys Pro Lys Phe Val Ala Asn Ala Gly Leu Lys Val
           35                  40                  45

AAG GCA AGC GCC AGT GCC CCT CCT AAG ATC AAT GGT TCC TCG GTC GGT      971
Lys Ala Ser Ala Ser Ala Pro Pro Lys Ile Asn Gly Ser Ser Val Gly
       50                  55                  60

CTA AAG TCC GGC AGT CTC AAG ACT CAG GAA GAT ACT CCT TCG GTG CCT     1019
Leu Lys Ser Gly Ser Leu Lys Thr Gln Glu Asp Thr Pro Ser Val Pro
```

-continued

```
            65                 70                  75
CCT CCG CGG ACG TTT ATC AAC CAG TTG CCT GAT TGG AGT ATG CTT CTT    1067
Pro Pro Arg Thr Phe Ile Asn Gln Leu Pro Asp Trp Ser Met Leu Leu
 80              85                   90                  95

GCT GCA ATC ACT ACT GTC TTC TTG GCA GCA GAG AAG CAG TGG ATG ATG    1115
Ala Ala Ile Thr Thr Val Phe Leu Ala Ala Glu Lys Gln Trp Met Met
                100                 105                 110

CTT GAC TGG AAA CCT AAG AGG CCT GAC ATG CTT GTG GAC CCG TTC GGA    1163
Leu Asp Trp Lys Pro Lys Arg Pro Asp Met Leu Val Asp Pro Phe Gly
            115                 120                 125

TTG GGA AGT ATT GTC CAG GGT GGG CTT GTG TTC AGG CAA AAT TTT TCT    1211
Leu Gly Ser Ile Val Gln Gly Gly Leu Val Phe Arg Gln Asn Phe Ser
        130                 135                 140

ATT AGG TCC TAT GAA ATA GGC GCT GAT CGC ACT GCA TCT ATA GAG ACG    1259
Ile Arg Ser Tyr Glu Ile Gly Ala Asp Arg Thr Ala Ser Ile Glu Thr
    145                 150                 155

GTG ATG AAC CAC TTG CAG GTACTGGTGC ATCCTGCAGT TAAACTATTC           1307
Val Met Asn His Leu Gln
160             165

AATTCATGAA ATGCTTATGT CCAGTAACCG AGCCATACTT GACTATGGCT TACCAAATTT   1367

AAGGGTGAAT TTGAGAAAGA AGGGTTGTAC TGCATTCCTC TCTATTGTCA TGAGGTGATT   1427

CAATATAGGT TTACCTCGTG TCAATTTTTA ACATATGCAT TCATTTCATG ACGCTTTGGC   1487

TTCTTATGGT GAGCTTTGTC ATGTCGAGTC AATGGAAGGA TCATCTGCTC TACTATATTA   1547

TTATTGAATT TAGGCATGAT GAAAGTTTAT GTGGAACTTA GTTACTTCTG TGATAGAAAA   1607

CCAAGAAAGG AAAGCTTCCT CTTCCCTTTA ACCTTAAAAA AAAAACCTTA ACTCTCATTT   1667

CAATTGAAAA CTGGATTAGT TTTCAGATAT GTATATAATG ATTAAACATT TGCATTAGTT   1727

TGCTCATAAT TTTGGTTGAA TTCATTGTCT TTGTCCTGTG CTTTTTTTTT CTTTTACAG    1786

GAA ACG GCT CTC AAT CAT GTT AAG AGT GCT GGG CTT CTT AAT GAC GGC    1834
Glu Thr Ala Leu Asn His Val Lys Ser Ala Gly Leu Leu Asn Asp Gly
                170                 175                 180

TTT GGT CGT ACT CCT GAG ATG TTT AAA AGG GAC CTC ATT TGG GTT GTC    1882
Phe Gly Arg Thr Pro Glu Met Phe Lys Arg Asp Leu Ile Trp Val Val
            185                 190                 195

GCG AAA ATG CAG GTC ATG GTT AAC CGC TAT CCT ACT    TG GTAAGTTTGT    1930
Ala Lys Met Gln Val Met Val Asn Arg Tyr Pro Thr    Trp
        200                 205                 210

CACTAGCTTT TTACTTTGCG GTACTTCGAG GCTTTATAAA ATTTTGTGTC AATGTAGCTG   1990

TAATGTATAT CATATTGTAA TGAGTGCTCA CTGTTACCTT CCTTGTGATA TGGTGTTTCA   2050

TTTCAATATA ACACCGATGA CTACAAATCT CCTTTATGTT GTGGAACCTA AGGGCCCTGT   2110

CTGATTCAG G GGT GAC ACG GTT GAA GTG AAT ACT TGG GTT GCC AAG TCA    2159
            Gly Asp Thr Val Glu Val Asn Thr Trp Val Ala Lys Ser
                            215                 220

GGG AAA AAT GGT ATG CGT CGT GAT TGG CTC ATA AGT GAT TGC AAT ACA    2207
Gly Lys Asn Gly Met Arg Arg Asp Trp Leu Ile Ser Asp Cys Asn Thr
225                 230                 235

GGA GAA ATT CTA ACT AGA GCT TCA   AG GTATGATGCA CTGTTTTGTA          2253
Gly Glu Ile Leu Thr Arg Ala Ser   Ser
240                 245

GTTTATGTTC CTGTACTTTC TAGTGGTCAG ATTTGAGAGC ATTCAATCGG GATATTTTAC   2313

GGTGAAAGTC GAATTAAATT ACCCTTTTAT TATTGCAG C GTG TGG GTC ATG ATG    2367
                                            Val Trp Val Met Met
                                                    250

AAT CAA AAG ACA AGA AAA TTG TCA AAA ATT CCA GGT GAG GTT CGA CAT    2415
Asn Gln Lys Thr Arg Lys Leu Ser Lys Ile Pro Gly Glu Val Arg His
```

```
                   255                 260                 265
GAG ATA GAG CCT CAT TTT ATA GAC TGT GCT CCC GTC ATT GAA GAC GAT       2463
Glu Ile Glu Pro His Phe Ile Asp Cys Ala Pro Val Ile Glu Asp Asp
270                 275                 280                 285

GAC CGG AAA CTC CGC AAG CTG GAT GAG AAG ACT GCT GAC TCC ATC CGC       2511
Asp Arg Lys Leu Arg Lys Leu Asp Glu Lys Thr Ala Asp Ser Ile Arg
                290                 295                 300

AAG GGT CTA ACT GTAAGGCCAT ATTTTACACT TTAATAGTGG CTTGCATTGC           2563
Lys Gly Leu Thr
            305

TATATAAAAA AATCATGCTT CTTAGACGAT TTTCCTCTTC GCAATTTGTA G CCG AAG      2620
                                                        Pro Lys

TGG AAT GAC TTG GAT GTC AAT CAG CAT GTC AAC AAC GTG AAG TAC ATC       2668
Trp Asn Asp Leu Asp Val Asn Gln His Val Asn Asn Val Lys Tyr Ile
            310                 315                 320

GGG TGG ATT CTC GAG GTAACTTTTT AACCTGTTAG CTGAATATGT GTGTATCTCG       2723
Gly Trp Ile Leu Glu
        325

ATAAGATATA TGAACGTAGA TATTGACCCA AGTAACTGCT AGCACATCAT ATGTCCCTGA     2783

AGTCCATTTA CAGTTATCAT ATTGCTAAAC TAATTATGCT GTTTCCTACA TAAACAATGT     2843

GCCAATGTTC GTTGCAG AGT ACT CCA CAA GAA GTT CTG GAG ACC CAA GAG        2893
                Ser Thr Pro Gln Glu Val Leu Glu Thr Gln Glu
                                330                 335

TTA TCT TCC CTT ACC CTG GAA TAC AGG CGG GAA TGC GGA AGG GAG AGC       2941
Leu Ser Ser Leu Thr Leu Glu Tyr Arg Arg Glu Cys Gly Arg Glu Ser
340                 345                 350                 355

GTG CTG GAG TCC CTC ACT GCT GTG GAC TCC TCT GGA AAG GGC TTT GGG       2989
Val Leu Glu Ser Leu Thr Ala Val Asp Ser Ser Gly Lys Gly Phe Gly
                360                 365                 370

TCC CAG TTC CAA CAC CTT CTG AGG CTT GAG GAT GGA GGT GAG ATC GTG       3037
Ser Gln Phe Gln His Leu Leu Arg Leu Glu Asp Gly Gly Glu Ile Val
            375                 380                 385

AAG GGG AGA ACT GAG TGG CGA CCC AAG ACT GCA GGT GTC AAT GGG GCA       3085
Lys Gly Arg Thr Glu Trp Arg Pro Lys Thr Ala Gly Val Asn Gly Ala
        390                 395                 400

ATA GCA TCC GGG GAG ACC TCA CAT GGA GAC TCT TAGAAGGGAG CCCCGGTCCC     3138
Ile Ala Ser Gly Glu Thr Ser His Gly Asp Ser
    405                 410

TTTCGAGTTC TGCTTTCTTT ATTGTCGGAT GAGCTGAGTG AACGGCAGGT AAGGTAGTAG     3198

CAATCAGTGG ATTGTGTAGT TTATTTGCTG TTTTTCACTT CGGCTCTCTT GTATAATATC     3258

ATGGTCTTCT TTGTGTTCTC GCATGTTTCG GGCTGATTTA TATATTATAT TCTTTCTATT     3318

TGTTTCAAGG TGAGTAGCGA GTTGTAATTA TTTATTTTGT CGTTAAATTT TCAAATGAAA     3378

GTACTTATGT GAACTGCATC GCCTTCCCTC AGAAGGTATC ATAATGAATT GTTACCATGT     3438

TGCTGCGCTG CGAGTCTGTT ACTTGTCATA TGCCGGTGTG GTTTGGTTTG GTGTGCTGTT     3498

CTGTTCTGTG TTGGAGTGGC TTAATTCGGA TAATATGTTT GTTTTATCAC CAGGGAGCAC     3558

AAGAAACCGC AAACAAGATA AGACACTGCT CATGGCTACA TTTGCTTAAC CTAGTAGGAC     3618

CAAAAGCAAC TCGAAAATCG AAAATGGGTG ATCATAGATT GATCTATGTT AAATTGTAAC     3678

CAACCTTTTG AAATTAATGA TGTTGATTCT TTGGTTGAGG AACATTTTGC TTCCTCAAAT     3738

TCATTGTATT TTGTTGCTTC ATTCAATGTG GTTTAATTTA ACCAGAGTTA TATTGTTCAT     3798

TTATTTTCTC CTTCCCCTTT TTAGTAGATA CATTGCCCCG GCTTCGCCCG GATATGCTAC     3858

TATCGTATAT TATTTAATTA CAAACTATAT ATATATGTAT ATGTACATAT CACTTTCGAT     3918

CAATTGTTAA ATAATAATA AACATTTAGT CACGATCATA AAATCATATA AAGTTGGTA      3978
```

```
CAATTAGAGG TTGTGAAAGT TGGTACAATT AGAGGTCGTG AACTATGAAC AAAGAAATAC        4038

ATATATCAAA GAAATACATA TATCAAAGCT TAAATGATCT TGCTCAAGAT ATTATAATAT        4098

ATATTGTGCT CTGTATAATA TAAGTAATAT ATATTGTGTG CTCTATACCA CATCTTCAGA        4158

CACGAAGAAG GTTTCCAACT TAAAGGAAAG AATGTGTTCC TGTAAAGTTT TGCAAGAAAA        4218

TAACCTACGT AAAGACTTTG AAAAGTATGC CGTTGTGATA AAAGAACTCG CAACAATATT        4278

AATTGTCGAA GATTCGAACC ATGCAAACTG AAAGCCTATA TGAGGAATAC ATCACGAGAA        4338

AAAATATTAA TAGCATAGCA AAAGAAAGAG AAAGTCAGAA TTTCTCTACC CAATATCGTT        4398

GAAACATGCG ATGGTAGAGC AACACACAGG AGCGGTAAGA ACCGACGAAG GAGTTGGTGT        4458

AAGATAAATA AACATTCAAA ATATCAATTA AATAAACTAT CAAGATATGG TGACACTATC        4518

GATTAGACGC GAAACGCCTT TAACAGAGGA TATTGCGCAA GTTCCTCTAC CAACTAATTG        4578

TGACATATCT CACATCCCGA TGTCTGATGA TACAAAAGAT CCCGAGAATC ACAACCGGCG        4638

GTACC                                                                  4643
```

(2) INFORMATION FOR SEQ ID NO: 7:

(i) SEQUENCE CHARACTERISTICS:
        (A) LENGTH: 5467 Base pairs
        (B) TYPE: nucleic acid
        (C) STRANDEDNESS: double stranded
        (D) TOPOLOGY: linear (ii) MOLECULE TYPE:: DNS (genomic)

(iii) HYPOTHETICAL: No (iii) ANTI-SENSE: No (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClTEg16

(ix) FEATURE:
        (A) NAME/KEY: CDS
        (B) LOCATION: join(3294..3779, 4045..4178, 4282..4395, 4512
           ..4680, 4767..4835, 5012..5275)

(ix) FEATURE:
        (A) NAME/KEY: Startcodon
        (B) LOCATION: 3294..3296

(ix) FEATURE:
        (A) NAME/KEY: exon II
        (B) LOCATION: 3284..3779

(ix) FEATURE:
        (A) NAME/KEY: intron II
        (B) LOCATION: 3780..4044

(ix) FEATURE:
        (A) NAME/KEY: exon III
        (B) LOCATION: 4045..4178

(ix) FEATURE:
        (A) NAME/KEY: intron III
        (B) LOCATION: 4179..4281

(ix) FEATURE:
        (A) NAME/KEY: exon IV
        (B) LOCATION: 4282..4395

(ix) FEATURE:
        (A) NAME/KEY: intron IV
        (B) LOCATION: 4396..4511

(ix) FEATURE:
        (A) NAME/KEY: exon V
        (B) LOCATION: 4512..4680

(ix) FEATURE:
        (A) NAME/KEY: intron V
        (B) LOCATION: 4681..4766

(ix) FEATURE:
        (A) NAME/KEY: exon VI
        (B) LOCATION: 4767..4835

(ix) FEATURE:
        (A) NAME/KEY: intron VI
        (B) LOCATION: 4836..5011

(ix) FEATURE:
        (A) NAME/KEY: exon VII
        (B) LOCATION: 5012..5275

(ix) FEATURE:
        (A) NAME/KEY: Stopcodon
        (B) LOCATION: 5276..5278

(xi) SEQUENCE DESCRIPTION: SEQ ID NO: 7:

| | | | | | |
|---|---|---|---|---|---|
| GTCGACTCGA | TCCACCCAAC | TTAATGCAAG | TGGCTCTTAA | ACTCTTGCTT | GTTTGCTTGC | 60 |
| TGCACTTGTC | ATGCAGGTTG | GTGGAATCTA | TGTGAGGCTG | TTCTTGAAAG | ACCCCAAGTT | 120 |
| TCCTCTCCGA | AATCCGAAGA | GGTTCCTTGA | AGGTCTCCTG | GATCAGTATC | TATCAGCAGT | 180 |
| GGCTGCAACA | CACTATGAAA | CGCAAGTGGA | CCCCGAGCTT | CCCTTGCTTT | TATCAGCTGC | 240 |
| CCTAGTTTCT | TTACTGCGAG | TTCACCCTGC | ACTCGCTGAT | CATGTGGGTT | ATCTCGGCTA | 300 |
| TGTGCCTAAG | CTTGTTGCTG | CTGTTGCCTA | TGAAAGTAGA | AGAGAAACAA | TGTCCTCAGT | 360 |
| GGAGGAGAAT | AATGGCCACG | CAGACAGAGC | AGCCTATGAG | CCTGGTGATG | GGTTAGAACA | 420 |
| ACCCACTCAG | ACCCCACGAG | AGCGAGTCCG | ACTCAGCTGC | TTACGTGTTT | TGCATCAGCT | 480 |
| TGCAGCGAGT | ACAACTTGTG | CTGAAGCTAT | GGCTGCAACT | AGTGTTGGGA | CACCACAGGT | 540 |
| AGATCTTATT | TCTCGTATAT | GTATATGCAT | TGGTGTCTGC | AATTTACATG | ATTAGCTAAG | 600 |
| AAGAATGTTC | CTGATATATG | TCAAAGATTC | TTCCGAGTTG | AATGCCCTGA | CAGGTTCATG | 660 |
| CATACCTTGA | GTTGCAGGTT | GTTCCAATTC | TAATGAAAGC | AATAGGCTGG | CAAGGCGGAA | 720 |
| GTATATTAGC | CCTTGAGACA | CTGAAACGGG | TTGTTGTCGC | TGGAAATCGG | GCTAGGGATG | 780 |
| CCCTGGTGGC | TCAAGGACTC | AAGTAAGTTT | ATTATCGGAT | ACAGGGCCTT | CCATACTTCG | 840 |
| ATAGAAGTTC | ATTCTCGTGT | CTGATTGAGT | GAAATTTTCA | GGGCTGGTCT | AGTTGAAGTC | 900 |
| CTTCTCGGGC | TTCTTGACTG | GAGAGCTGGA | GGAAGACATG | GACTCTGTGC | TCAGATGAAG | 960 |
| TGAACGAATC | TGAAGCATCT | ATTGGAAGGG | TTCTTGCCAT | AGAGGTCAGG | ATAGTTAACT | 1020 |
| TTATTTTGTC | TGCAGTATCG | TGACATTGTT | GCCTCACGAT | ATGCCGTTAA | TTTTTTGACC | 1080 |
| GCCAAACACG | GGTGTAAAAA | AAAAGTATC | TTAAATGTAT | GACTCAGGTT | TATCACGTCA | 1140 |
| TTTGCAACCG | AAGGGGCCCA | TTGTACTAAA | GTGCGTGAAC | TGCTGGATTC | GTCTGATGTA | 1200 |
| AGTTACCTCA | GCTTTCTTCT | GTTGTGTCTT | TATCCTGCAA | ACCTTTTCAT | GCAGTTGGCG | 1260 |
| ATATCTTAGG | GCCGGCATGG | TGGTTGCTCG | TTGCTTGATA | TTATAGTCGA | GTTAGATATT | 1320 |
| GTGATTCCAG | TAATGTAATA | TTTTGCACTT | GCATGTTGCC | AATGGTCATA | ATCAGTGTTG | 1380 |
| TCTAGAGAAT | AGTATTTGGA | TCTTTTCTAA | ATATCGAGTT | CTGATATGCT | AATCCTAAAT | 1440 |
| CTTATCTTTT | TAACCTCTCT | TTTCTTTGAT | TGTTTTCAGG | TTTGGGGTGC | ATACAAAGAC | 1500 |
| CAAAAGCACG | ACCTCTTCCT | TCCATCAAGT | GCTCAGTCCG | CTGCTGGAGT | GGCTGGCTTG | 1560 |
| ATTGAGAACT | CGTCCTCTCG | ACTCACGTAT | GCCCTCACAG | CCCCGCCTCC | CACATCATCT | 1620 |

```
CCTCCATCAT ACTCCAATGG CAACGAAGAT ATCTTCCATC TGTAAAGACA AGTCCTGTAG    1680

TGATATAAAA TAGCTCATTT CTGTACAGGT TTTCGTTGGC TTTAGTCATC AGGCTTTCGA    1740

GTTTGTTCAT GTTTCGTTTC TTCTTACATC ATATATATCC TTGGGGGCGT TGCAGATTGG    1800

CATGGCGTTT TCATTTTCAA TCTCCTGATA TCAAACCTTG GAATTTATTC CTTTGCTTCA    1860

TTTTTACTCC ACACTCCACT GTAAAGATCA CTCGATCATT TATGTGTAAA TTGAGGTTCT    1920

GGTTGCTTTC TGCACATTTT TTATATGATC ATTTTCAATG GTCACTATTT CTTCTGTATC    1980

ACTAAAGAGC CTATATTAAT AAATAAAGAT TCATCATCAT CCCATTCATA TATTTGCTCT    2040

ATTCCTATGT ATAATATTAT TTTCATTCAA AAATTGTTTG TGAATTCCGA CTTCAATGAG    2100

ATTCTAAATT TAGAATCCCA TGCCAACTAA GATAGACTCT AATGTAGATT CAAATTATTT    2160

TGAAGACTCT AAATTGACAT TTAAAAAGTT TTTATGGAGA TGTTCTAAGC GGCACCTTCA    2220

TAAGAATTAA AAATACTAAA TAAATTTTTT AGTGAAAGGT CAAATGTGCC TATAATAAGT    2280

AAAGAAAGT TATTATTAAT GATTTATTAA AGTAATATCT CTTTTTTTTT TTTTTACAAG    2340

TTCTAATATT TGAAGATAAA AAAAAAAAAA AAATTCACAG TGAAAGCTGA AATGAAACTC    2400

AAACTCCCCT GACACCTTTC GCTTCGCACT GTCTCTGTCT TCTAAAATCC ACGAGTCGGG    2460

AAAGAAAGAT TCAATTTGAT TCACTGTTGA CGAAGCTGAA GATCACAAAT TCCAACCTC    2520

AGGATACCTC TTACCTTTGC CTTTGCCTTT GCTTTTTTCT TTGCCTCTCT TCTCTTCATT    2580

CGGCTCTGTC CCTTCCCCTC TTCGCGTTGC TTCTTCTATT GAACTGTTGT CTGTTCATGT    2640

CACCGTTTGC CCTTCCACTT CAGCTATATG GCCCTCTCTC TCTCGCACTA CGTGTCTGAT    2700

CTGCAGTTTC CATTCCCGCT TCTGTCTCCT TCCTTCACAA GACTTCATTT GCATACACCA    2760

CTGACCTGAG CCCCACCCAC CCTCCGTCAC CCAGTGTCAC TCTTCTGCAA ACCCATCTGC    2820

TCTCTTCTTT TTCCCTCCAC CGTAGCCCAT AGAAACCACC TTCGCCCTTT TCCTCCTCGT    2880

GTTGATCGGA CCTCATCATG TCTCCTTTCT TTCTGCCAAA TGTCTGGCCT TTCTTCTCGC    2940

GCCCACTTTT GTTTTTAATG TTATGCTCCC AGCCACGTTC CTTCCATTCT CTGCTCTCCT    3000

CATGGCTCCT TCCGGGCCAC CATCAGAGTC CCCTTCTTTA TATGGCTTCC ATTTTCCTTC    3060

CTTGATGGAT ATCCCATCTT CATCTGTGTT TGCTGGATAC CATTTTCCCT GTATGTTCAG    3120

TTCATGCCAT GCATGTCTAT GCCTTTCTTT CCCCTTACTA CATTTGCTGT AACATTGTGT    3180

TGTGTTTTGT CATAAAGCTT TCATCTTTCC CTTCTGTTTG AATCCGAGGT TGTCTTTTTT    3240

ATGCATTTCA AGCTTCTGAT GACTGACCCT TTTGTGCTTT CAGGCGAACA AAC ATG       3296
                                                            Met
                                                            1

GTG GCT GCC GCA GCA AGC TCT GCA TTC TTC TCC TTT CCA ACC CCC GGA      3344
Val Ala Ala Ala Ala Ser Ser Ala Phe Phe Ser Phe Pro Thr Pro Gly
      5                  10                  15

ACC TCC CCC AAA CCC GGG AAG TTC GGC AAC TGG CCA TCG AGC CTG AGC      3392
Thr Ser Pro Lys Pro Gly Lys Phe Gly Asn Trp Pro Ser Ser Leu Ser
      20                  25                  30

GTC CCC TTC AAT CTC AAA TCA AAC CAC AAT GGT GGC TTT CAG GTT AAG      3440
Val Pro Phe Asn Leu Lys Ser Asn His Asn Gly Gly Phe Gln Val Lys
      35                  40                  45

GCA AAC GCC AGT GCT CAT CCT AAG GCT AAC GGT TCT GCA GTA AGT CTA      3488
Ala Asn Ala Ser Ala His Pro Lys Ala Asn Gly Ser Ala Val Ser Leu
 50              55                  60                          65

AAG GCT GGC AGC CTC GAG ACT CAG GAG GAC ACT TCA GCG CCG TCC CCT      3536
Lys Ala Gly Ser Leu Glu Thr Gln Glu Asp Thr Ser Ala Pro Ser Pro
              70                  75                  80

CCT CCT CGG ACT TTC ATT AAC CAG TTG CCT GAC TGG AAT ATG CTT CTG      3584
Pro Pro Arg Thr Phe Ile Asn Gln Leu Pro Asp Trp Asn Met Leu Leu
```

-continued

```
                      85                      90                      95
TCC GCA ATC ACG ACT GTC TTC GTT GCG GCT GAG AAG CAG TGG ACG ATG           3632
Ser Ala Ile Thr Thr Val Phe Val Ala Ala Glu Lys Gln Trp Thr Met
            100                     105                     110

CTT GAT CGG AAA TCT AAG AGG TCA GAC GTG CTC GTG GAA CCG TAT GTT           3680
Leu Asp Arg Lys Ser Lys Arg Ser Asp Val Leu Val Glu Pro Tyr Val
            115                     120                     125

CAG GAT GGT GTT TCG TTC AGA CAG AGT TTT TCG ATA AGG TCT TAC GAA           3728
Gln Asp Gly Val Ser Phe Arg Gln Ser Phe Ser Ile Arg Ser Tyr Glu
130                     135                     140                     145

ATT GGC GCT GAT CGA ACA GCC TCA ATA GAG ACG CTG ATG AAC CAT CTT           3776
Ile Gly Ala Asp Arg Thr Ala Ser Ile Glu Thr Leu Met Asn His Leu
                150                     155                     160

CAG GTACTGCATT GAAACTATTC AACCATAGCA TTGCTAGTGA TCTGTAAATG                3829
Gln

AGCCACGACT GACGATGACA TAGATACACC GAATTGCCAG TATATGTGTG TCCATTTTAA         3889

TTTAGAGCTG ATGTTATTAT AAGTTCATGA TGAGGTTGGT ATCTCAGGAT GAGATTTGTA         3949

AGGTTGATTC AAGGGAGGAA CCATAACATA TGTTTGATTG TATTTCCTCG TTAACTCCAT         4009

TGTCTTTGTT CTATGTTTTT TTTTTCTCTA AACAG GAA ACA TCT CTG AAT CAT            4062
                                      Glu Thr Ser Leu Asn His
                                                          165

TGT AAG AGT CTC GGT CTT CTC AAT GAC GGC TTT GGT CGT ACT CCT GAG           4110
Cys Lys Ser Leu Gly Leu Leu Asn Asp Gly Phe Gly Arg Thr Pro Glu
        170                     175                     180

ATG TGT AAG AGG GAC CTC ATT TGG GTG GTT ACG AAA ATG CAG GTA ATG           4158
Met Cys Lys Arg Asp Leu Ile Trp Val Val Thr Lys Met Gln Val Met
185                     190                     195                     200

GTG AAT CGC TAT CCT ACT  TG GTAAGTTTGT CTCTGCTTGT TTGTCTTATG              4208
Val Asn Arg Tyr Pro Thr  Trp
                    205

GTCCACAAAT CTCTCTTACG GTAATGGTTG TAAACATAGT GGAATGTAAT GGCATGTGTG         4268

ATCTATATGG TAG G GGT GAC ACT ATC GAG GTC ACT ACT TGG GTC TCC GAG          4318
                Gly Asp Thr Ile Glu Val Thr Thr Trp Val Ser Glu
                                210                     215

TCG GGA AAA AAC GGT ATG AGT CGT GAT TGG CTG ATA AGT GAT TGC CAT           4366
Ser Gly Lys Asn Gly Met Ser Arg Asp Trp Leu Ile Ser Asp Cys His
220                     225                     230                     235

TCG GGA GAA ATT CTT ATA AGA GCA ACG  AG GTAGACTTTT CTGGTTCTGA             4415
Ser Gly Glu Ile Leu Ile Arg Ala Thr  Ser
            240                     245

TTTTACATTC TTAAACCTTC TGATGTTCGA CTGAGAGCAG ACATTGGTA TGTTTTATAT          4475

TGAAAGTTGA GTCAAGTCAC TCTAATACTA TCGCAG C GTG TGG GCT ATG ATG             4527
                                         Val Trp Ala Met Met
                                                             250

AAT CAA AAG ACA AGA AGA TTG TCA AAA ATT CCA GAT GAG GTT CGA CAG           4575
Asn Gln Lys Thr Arg Arg Leu Ser Lys Ile Pro Asp Glu Val Arg Gln
                255                     260                     265

GAG ATA GTG CCT TAT TTT GTG GAC TCT GCT CCT GTC ATT GAA GAC GAT           4623
Glu Ile Val Pro Tyr Phe Val Asp Ser Ala Pro Val Ile Glu Asp Asp
            270                     275                     280

CGA AAA TTG CAC AAG CTT GAT GTG AAG ACG GGT GAT TCC ATT CGC AAT           4671
Arg Lys Leu His Lys Leu Asp Val Lys Thr Gly Asp Ser Ile Arg Asn
285                     290                     295

GGT CTA ACT GTAAGTCCCT ATATTTCAAT ATGAAATGTG GCGCGTTTCA                   4720
Gly Leu Thr
```

```
                                                         300
TGAAATATCA CATCTCTGAG GCGATCTATC TCTTCACGGT CTGTAG CCA AGG TGG          4775
                                                   Pro Arg Trp
AAT GAC TTT GAT GTC AAT CAG CAC GTT AAC AAT GTG AAG TAC ATT GCG        4823
Asn Asp Phe Asp Val Asn Gln His Val Asn Asn Val Lys Tyr Ile Ala
305                 310                 315                 320
TGG CTT CTC AAG GTACCCTTTT CATCATACAA ACAACTGATA TATATATCTG            4875
Trp Leu Leu Lys
CTCGCCCAAG TATCTGCTTG CTAGCACTTG AGATATTACT TAAATATCGT GGATTAGTAT      4935
TGCCCCGAGT TTGTCAATGC TTGATTTACA CAGTTCAGCT AAACAAATCT GTAATCTATA      4995
TGAATGCTTG TTGCAG AGT GTT CCA ACA GAA GTT TTC GAG ACC CAG GAG          5044
               Ser Val Pro Thr Glu Val Phe Glu Thr Gln Glu
                325                 330                 335
CTA TGC GGC CTC ACC CTT GAG TAT AGG CGG GAA TGC AGA AGG GAC AGT        5092
Leu Cys Gly Leu Thr Leu Glu Tyr Arg Arg Glu Cys Arg Arg Asp Ser
                340                 345                 350
GTG CTG GAG TCC GTG ACC GCT ATG GAT CCC TCA AAA GAG GGA GAC CGG        5140
Val Leu Glu Ser Val Thr Ala Met Asp Pro Ser Lys Glu Gly Asp Arg
                355                 360                 365
TCT CTG TAC CAG CAC CTT CTT CGG CTT GAG AAT GGG GCT GAT ATC GCC        5188
Ser Leu Tyr Gln His Leu Leu Arg Leu Glu Asn Gly Ala Asp Ile Ala
                370                 375                 380
TTG GGT AGA ACC GAG TGG CGG CCG AAG AAT GCA GGA GCC AAT GGG GCA        5236
Leu Gly Arg Thr Glu Trp Arg Pro Lys Asn Ala Gly Ala Asn Gly Ala
385                 390                 395
GTA TCA ACA GGA AAG ACT TCA AAT GGA AAT TCT GTC TCT TAGAAGTGGC         5285
Val Ser Thr Gly Lys Thr Ser Asn Gly Asn Ser Val Ser
400                 405                 410
TGGGGGCCTT TCCAAGTTGT GCGTTTATTT TTTCTGAAAG AAGGGAATGT TGCTGCAATC      5345
AGTAAACTGT GTAGTTCGTT TGCAGTTTGT ATATTAACAC GGTCGGTCGT GTTTGTATTT      5405
GCTAAGACAA ATAGCACATT CATCGTTACA TATCGTAGAT CTCGAACAGT ACTGTCAAGC      5465
AT                                                                    5467
```

(2) INFORMATION FOR SEQ ID NO: 8:

(i) SEQUENCE CHARACTERISTICS:
        (A) LENGTH: 530 Base pairs
        (B) TYPE: nucleic acid
        (C) STRANDEDNESS: double stranded
        (D) TOPOLOGY: linear (ii) MOLECULE TYPE:: c-DNA (iii) HYPOTHETICAL: No (iii) ANTI-SENSE: No (vi) ORIGINAL SOURCE:
        (A) ORGANISM: Umbellularia californica (vii) IMMEDIATE SOURCE:
        (A) LIBRARY: c-DNA Bank ZAP (ix) FEATURE:
        (A) NAME/KEY: PCR-Product PCR 42
        (B) LOCATION: 1..530

(ix) FEATURE:
        (A) NAME/KEY: Oligonucleotide primer
        (B) LOCATION: 1..23

(ix) FEATURE:
        (A) NAME/KEY: CDS
        (B) LOCATION: 1..327

(ix) FEATURE:
    (A) NAME/KEY: Stopcodon
    (B) LOCATION: 328..330

(xi) SEQUENCE DESCRIPTION: SEQ ID NO: 8:

| | | | | | | | | | | | | | | | | |
|---|---|---|---|---|---|---|---|---|---|---|---|---|---|---|---|---|
|TGG|AAT|GAC|TTG|GAT|GTG|AAC|CAG|CAC|GTT|AAC|AAT|GTG|AAG|TAC|ATT|48|
|Trp|Asn|Asp|Leu|Asp|Val|Asn|Gln|His|Val|Asn|Asn|Val|Lys|Tyr|Ile| |
|1| | | |5| | | | |10| | | | |15| | |

```
GCG TGG CTT CTC AAG AGT GTT CCA ACA GAA GTT TTC GAG ACC CAG GAG      96
Ala Trp Leu Leu Lys Ser Val Pro Thr Glu Val Phe Glu Thr Gln Glu
             20                  25                  30

CTA TGC GGC CTC ACC CTT GAG TAT AGG CGG GAA TGC AGA AGG GAC AGT     144
Leu Cys Gly Leu Thr Leu Glu Tyr Arg Arg Glu Cys Arg Arg Asp Ser
         35                  40                  45

GTG CTG GAG TCC GTG ACC GCT ATG GAT CCC TCA AAA GAG GGA GAC CGG     192
Val Leu Glu Ser Val Thr Ala Met Asp Pro Ser Lys Glu Gly Asp Arg
 50                  55                  60

TCT CTG TAC CAG CAC CTT CTT CGG CTT GAG AAT GGG GCT GAT ATC GCC     240
Ser Leu Tyr Gln His Leu Leu Arg Leu Glu Asn Gly Ala Asp Ile Ala
 65                  70                  75                  80

TTG GGT AGA ACC GAG TGG CGG CCG AAG AAT GCA GGA GCC AAT GGG GCA     288
Leu Gly Arg Thr Glu Trp Arg Pro Lys Asn Ala Gly Ala Asn Gly Ala
                 85                  90                  95

GTA TCA ACA GGA AAG ACT TCA AAT GGA AAT TCT GTC TCT TAGAAGTGGC      337
Val Ser Thr Gly Lys Thr Ser Asn Gly Asn Ser Val Ser
             100                 105

TGGGGGCCTT TCCAAGTTGT GCGTTTATTT TTTCTGAAAG AAGGGAATGT TGCTGCAATC   397

AGTAAACTGT GTAGTTCGTT TGCAGTTTGT ATATTAACAC GGTCGGTCGT GTTTGTATTT   457

GCTAAGACAA ATAGCACATT CATCGTTACA AAAAAAAAAA AAAAAAAAAG CTTCCTAGGT   517

TCGAACAGCG ACC                                                      530
```

(2) INFORMATION FOR SEQ ID NO: 9:

(i) SEQUENCE CHARACTERISTICS:
        (A) LENGTH: 23 Base pairs
        (B) TYPE: nucleic acid
        (C) STRANDEDNESS: double stranded
        (D) TOPOLOGY: linear (ii) MOLECULE TYPE:: DNA (iii) HYPOTHETICAL: No (iii) ANTI-SENSE: No (vii) IMMEDIATE SOURCE:
        (B) CLONE: 5'- Primer 3532

(xi) SEQUENCE DESCRIPTION: SEQ ID NO: 9:

TGGAAYGAYY TNGAYGTNAA YGA                                            23

(2) INFORMATION FOR SEQ ID NO: 10:

(i) SEQUENCE CHARACTERISTICS:
        (A) LENGTH: 41 Base pairs
        (B) TYPE: nucleic acid
        (C) STRANDEDNESS: double stranded
        (D) TOPOLOGY: linear (ii) MOLECULE TYPE:: DNA (iii) HYPOTHETICAL: No (iii) ANTI-SENSE: No (vii) IMMEDIATE SOURCE:
  (B) CLONE: 3'- Primer 2740

(xi) SEQUENCE DESCRIPTION: SEQ ID NO: 10:

TTTTTTTTTT TTTTTTTTCG AAGGATCCAA GCTTGTCGAC T                  41

(2) INFORMATION FOR SEQ ID NO:11:

(i) SEQUENCE CHARACTERISTICS:
    (A) LENGTH: 366 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:11:

```
Met Leu Lys Leu Ser Cys Asn Val Thr Asn His Leu His Thr Phe Ser
 1               5                  10                  15

Phe Phe Ser Asp Ser Ser Leu Phe Ile Pro Val Asn Arg Thr Leu
            20                  25                  30

Ala Val Ser Ser Gln Pro Arg Lys Pro Ala Leu Asp Pro Leu Arg
        35                  40                  45

Ala Val Ile Ser Ala Asp Gln Gly Ser Ile Ser Pro Val Asn Ser Cys
50                  55                  60

Thr Pro Ala Asp Arg Phe Arg Ala Gly Arg Leu Met Glu Asp Gly Tyr
65                  70                  75                  80

Ser Tyr Lys Glu Lys Phe Ile Val Arg Ser Tyr Glu Val Gly Ile Asn
                85                  90                  95

Lys Thr Ala Thr Val Glu Thr Ile Ala Asn Leu Leu Gln Glu Val Ala
            100                 105                 110

Cys Asn His Val Gln Lys Cys Gly Phe Ser Thr Asp Gly Phe Ala Thr
            115                 120                 125

Thr Leu Thr Met Arg Lys Leu His Leu Ile Trp Val Thr Ala Arg Met
            130                 135                 140

His Ile Glu Ile Tyr Lys Tyr Pro Ala Trp Ser Asp Val Val Glu Ile
145                 150                 155                 160

Glu Thr Trp Cys Gln Ser Glu Gly Arg Ile Gly Thr Arg Arg Asp Trp
                165                 170                 175

Ile Leu Arg Asp Ser Ala Thr Asn Glu Val Ile Gly Arg Ala Thr Ser
            180                 185                 190

Lys Trp Val Met Met Asn Gln Asp Thr Arg Arg Leu Gln Arg Val Thr
            195                 200                 205

Asp Glu Val Arg Asp Glu Tyr Leu Val Phe Cys Pro Arg Glu Pro Arg
210                 215                 220

Leu Ala Phe Pro Glu Glu Asn Asn Ser Ser Leu Lys Lys Ile Pro Lys
225                 230                 235                 240

Leu Glu Asp Pro Ala Gln Tyr Ser Met Leu Glu Leu Lys Pro Arg Arg
                245                 250                 255

Ala Asp Leu Asp Met Asn Gln His Val Asn Asn Val Thr Tyr Ile Gly
            260                 265                 270

Trp Val Leu Glu Ser Ile Pro Gln Glu Ile Ile Asp Thr His Glu Leu
            275                 280                 285

Gln Val Ile Thr Leu Asp Tyr Arg Arg Glu Cys Gln Gln Asp Asp Ile
            290                 295                 300

Val Asp Ser Leu Thr Thr Ser Glu Ile Pro Asp Asp Pro Ile Ser Lys
305                 310                 315                 320
```

```
Leu Thr Gly Thr Asn Gly Ser Ala Thr Ser Ser Ile Gln Gly His Asn
            325                 330                 335

Glu Ser Gln Phe Leu His Met Leu Arg Leu Ser Glu Asn Gly Gln Glu
            340                 345                 350

Ile Asn Arg Gly Arg Thr Gln Trp Arg Lys Lys Ser Ser Arg
            355                 360                 365
```

(2) INFORMATION FOR SEQ ID NO:12:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Met Ala Thr Thr Ser Leu Ala Ser Ala Phe Cys Ser Met Lys Ala Val
 1               5                  10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
            35                  40                  45

Thr Lys Phe Ser Tyr Thr Glu Ser Leu Lys Arg Leu Pro Asp Trp Ser
 50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
            85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
            115                 120                 125

Val Met Asn His Met Gln Glu Ala Thr Leu Asn His Ala Lys Ser Val
            130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
                180                 185                 190

Gly Asn Asn Gly Met Arg Arg Asp Phe Leu Val Arg Asp Cys Lys Thr
            195                 200                 205

Gly Glu Ile Leu Thr Arg Cys Thr Ser Leu Ser Val Leu Met Asn Thr
            210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
            275                 280                 285

Leu Lys Tyr Val Ala Trp Val Phe Glu Thr Val Pro Asp Ser Ile Phe
            290                 295                 300

Glu Ser His His Ile Ser Ser Phe Thr Leu Glu Tyr Arg Arg Glu Cys
```

```
                      305                 310                 315                 320
Thr Arg Asp Ser Val Leu Arg Ser Leu Thr Thr Val Ser Gly Gly Ser
                    325                 330                 335

Ser Glu Ala Gly Leu Val Cys Asp His Leu Leu Gln Leu Glu Gly Gly
                340                 345                 350

Ser Glu Val Leu Arg Ala Arg Thr Glu Trp Arg Pro Lys Leu Thr Asp
                355                 360                 365

Ser Phe Arg Gly Ile Ser Val Ile Pro Ala Glu Pro Arg Val
                370                 375                 380

(2) INFORMATION FOR SEQ ID NO:13:

(i) SEQUENCE CHARACTERISTICS:
        (A) LENGTH: 389 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Met Leu Ser Arg Pro Leu Pro Thr Thr Ala Ala Ala Thr Thr Thr
 1               5                  10                  15

Thr Asn Asn Cys Asn Gly Val Asn Ser Arg Gly Ala Leu Pro His Ser
                20                  25                  30

Arg Ser Val Gly Phe Ala Ser Ile Arg Lys Arg Ser Thr Gly Ser Leu
             35                  40                  45

Cys Asn Ser Pro Pro Arg Thr Val Ala Pro Val Met Ala Val Arg Thr
         50                  55                  60

Gly Glu Gln Pro Thr Gly Val Ala Val Gly Leu Lys Glu Ala Glu Ala
 65                  70                  75                  80

Glu Val Glu Lys Ser Leu Ala Asp Arg Leu Arg Met Gly Ser Leu Thr
                 85                  90                  95

Glu Asp Gly Leu Ser Tyr Lys Glu Arg Phe Ile Ile Arg Cys Tyr Glu
             100                 105                 110

Val Gly Ile Asn Lys Thr Ala Thr Val Glu Thr Ile Ala Asn Leu Leu
         115                 120                 125

Gln Glu Val Gly Gly Asn His Ala Gln Ser Val Gly Phe Ser Thr Asp
130                 135                 140

Gly Phe Ala Thr Thr Thr Thr Met Arg Lys Leu His Leu Ile Trp Val
145                 150                 155                 160

Thr Ser Arg Met His Ile Glu Ile Tyr Arg Tyr Pro Ala Trp Ser Asp
                165                 170                 175

Val Val Glu Ile Glu Thr Trp Cys Gln Ser Glu Gly Arg Ile Gly Thr
            180                 185                 190

Arg Arg Asp Trp Ile Met Lys Asp His Ala Ser Gly Glu Val Ile Gly
        195                 200                 205

Arg Ala Thr Ser Lys Trp Val Met Met Asn Glu Asp Thr Arg Arg Leu
210                 215                 220

Gln Lys Val Asn Asp Asp Val Arg Asp Glu Tyr Leu Val Phe Cys Pro
225                 230                 235                 240

Lys Thr Pro Arg Leu Ala Phe Pro Glu Lys Asn Thr Ser Ser Leu Lys
                245                 250                 255

Lys Ile Ala Lys Leu Glu Asp Pro Ala Glu Tyr Ser Thr Leu Gly Leu
            260                 265                 270

Val Pro Arg Arg Ala Asp Leu Asp Met Asn Lys His Val Asn Asn Val
        275                 280                 285
```

```
Thr Tyr Ile Gly Trp Val Leu Glu Ser Ile Pro Gln Glu Val Ile Asp
        290                 295                 300
Thr His Glu Leu Gln Thr Ile Thr Leu Asp Tyr Arg Arg Glu Cys Gln
305                 310                 315                 320
His Asp Asp Ile Val Asp Ser Leu Thr Ser Ser Glu Ser Leu Leu Asp
                325                 330                 335
Asp Ala Ala Ile Ser Lys Leu Glu Gly Thr Asn Gly Ser Ser Val Pro
                340                 345                 350
Lys Lys Asp Glu Thr Asp Leu Ser Arg Phe Leu His Leu Leu Arg Ser
        355                 360                 365
Ser Gly Asp Gly Leu Glu Leu Asn Arg Gly Arg Thr Glu Trp Arg Lys
        370                 375                 380
Lys Pro Ala Lys Lys
385

(2) INFORMATION FOR SEQ ID NO:14:

(i) SEQUENCE CHARACTERISTICS:
        (A) LENGTH: 385 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Met Leu Ser Lys Gly Ala Pro Ala Pro Ala Val Ala Ala Met Tyr
1               5                   10                  15
Asn Ala Ser Ala Lys Asp Thr Thr Phe Ala Leu Thr His Ser Arg Ser
                20                  25                  30
Ile Gly Ser Val Ser Ile Arg Arg Arg Tyr Asn Val Phe Leu Cys Asn
                35                  40                  45
Ser Ser Ser Ser Arg Lys Val Ser Pro Leu Leu Ala Val Ala Thr
        50                  55                  60
Gly Glu Gln Pro Ser Gly Val Ala Ser Leu Arg Glu Ala Asp Lys Glu
65                  70                  75                  80
Lys Ser Leu Gly Asn Arg Leu Arg Leu Gly Ser Leu Thr Glu Asp Gly
                85                  90                  95
Leu Ser Tyr Lys Glu Lys Phe Val Ile Arg Cys Tyr Glu Val Gly Ile
                100                 105                 110
Asn Lys Thr Ala Thr Ile Glu Thr Ile Ala Asn Leu Leu Gln Glu Val
            115                 120                 125
Gly Gly Asn His Ala Gln Gly Val Gly Phe Ser Thr Asp Gly Phe Ala
        130                 135                 140
Thr Thr Thr Thr Met Arg Lys Leu His Leu Ile Trp Val Thr Ala Arg
145                 150                 155                 160
Met His Ile Glu Ile Tyr Arg Tyr Pro Ala Trp Ser Asp Val Ile Glu
                165                 170                 175
Ile Glu Thr Trp Val Gln Gly Glu Gly Lys Val Gly Thr Arg Arg Asp
                180                 185                 190
Trp Ile Leu Lys Asp Tyr Ala Asn Gly Glu Val Ile Gly Arg Ala Thr
            195                 200                 205
Ser Lys Trp Val Met Met Asn Glu Asp Thr Arg Arg Leu Gln Lys Val
        210                 215                 220
Ser Asp Asp Val Arg Glu Glu Tyr Leu Val Phe Cys Pro Arg Thr Leu
225                 230                 235                 240
```

-continued

```
Arg Leu Ala Phe Pro Glu Glu Asn Asn Asn Ser Met Lys Lys Ile Pro
            245             250                 255

Lys Leu Glu Asp Pro Ala Glu Tyr Ser Arg Leu Gly Leu Val Pro Arg
            260             265                 270

Arg Ser Asp Leu Asp Met Asn Lys His Val Asn Asn Val Thr Tyr Ile
        275             280                 285

Gly Trp Ala Leu Glu Ser Ile Pro Pro Glu Ile Ile Asp Thr His Glu
    290             295             300

Leu Gln Ala Ile Thr Leu Asp Tyr Arg Arg Glu Cys Gln Arg Asp Asp
305             310             315                     320

Ile Val Asp Ser Leu Thr Ser Arg Glu Pro Leu Gly Asn Ala Ala Gly
            325             330             335

Val Lys Phe Lys Glu Ile Asn Gly Ser Val Ser Pro Lys Lys Asp Glu
            340             345             350

Gln Asp Leu Ser Arg Phe Met His Leu Leu Arg Ser Ala Gly Ser Gly
        355             360             365

Leu Glu Ile Asn Arg Cys Arg Thr Glu Trp Arg Lys Lys Pro Ala Lys
    370             375             380

Arg
385
```